US011642670B2

(12) United States Patent
Cappi et al.

(10) Patent No.: US 11,642,670 B2
(45) Date of Patent: May 9, 2023

(54) METHODS OF IN SITU ANTIGEN RETRIEVAL OF A BIOLOGICAL SAMPLE AND IMAGING THEREOF

(71) Applicant: LUNAPHORE TECHNOLOGIES SA, Tolochenaz (CH)

(72) Inventors: Giulia Cappi, Lausanne (CH); Marta Comino, Lausanne (CH); Marco Ammann, Lausanne (CH); Diego Gabriel Dupouy, Préverenges (CH); Ata Tuna Ciftlik, Morges (CH)

(73) Assignee: LUNAPHORE TECHNOLOGIES SA, Lausanne (CH)

( * ) Notice: Subject to any disclaimer, the term of this patent is extended or adjusted under 35 U.S.C. 154(b) by 497 days.

(21) Appl. No.: 16/630,148

(22) PCT Filed: Jul. 11, 2018

(86) PCT No.: PCT/EP2018/068830
§ 371 (c)(1),
(2) Date: Jan. 10, 2020

(87) PCT Pub. No.: WO2019/012005
PCT Pub. Date: Jan. 17, 2019

(65) Prior Publication Data
US 2020/0353467 A1  Nov. 12, 2020

(30) Foreign Application Priority Data
Jul. 12, 2017  (EP) .................................... 17180896

(51) Int. Cl.
*B01L 3/00* (2006.01)
*B01L 7/00* (2006.01)
(Continued)

(52) U.S. Cl.
CPC .......... *B01L 3/502715* (2013.01); *B01L 7/52* (2013.01); *B01L 9/527* (2013.01); *C12Q 1/6825* (2013.01);
(Continued)

(58) Field of Classification Search
CPC ......... B01L 2200/027; B01L 2200/147; B01L 2300/0609; B01L 2300/0627;
(Continued)

(56) References Cited

U.S. PATENT DOCUMENTS 5,244,787 A    9/1993  Key et al.
6,649,368 B1  11/2003  Aghassi et al.
(Continued)

FOREIGN PATENT DOCUMENTS

CN    104245917 A    12/2014
CN    104284725 A    1/2015
(Continued)

OTHER PUBLICATIONS

Krenacs et al. Heat-induced antigen retrieval for immunohistochemical reactions in routinely processed paraffin sections. Methods Mol Biol. 2010;588:103-19. doi: 10.1007/978-1-59745-324-0_14. PMID: 20012825; PMCID: PMC7604828. (Year: 2010).*
(Continued)

*Primary Examiner* — Christine T Mui
*Assistant Examiner* — Jonathan Bortoli
(74) *Attorney, Agent, or Firm* — Nixon & Vanderhye P.C.

(57) ABSTRACT

The invention relates to a device and method for in situ temperature-induced antigen retrieval of samples wherein all steps are performed under a pressure higher than the atmospheric pressure on a sample immobilized on a sample support which can be further subjected to staining and imaging on the same sample support, optionally by cycle multiplexing that enables imaging of various molecular
(Continued)

targets through multi-molecular read-outs on the same sample in a rapid, highly sensitive and reliable manner.

6 Claims, 12 Drawing Sheets

(51) Int. Cl.
  *B01L 9/00* (2006.01)
  *C12Q 1/6825* (2018.01)
  *G01N 1/30* (2006.01)
  *G01N 1/31* (2006.01)
  *G01N 1/40* (2006.01)
  *G01N 33/53* (2006.01)

(52) U.S. Cl.
  CPC .................. *G01N 1/30* (2013.01); *G01N 1/31* (2013.01); *G01N 1/4022* (2013.01); *G01N 33/5306* (2013.01); *B01L 2200/027* (2013.01); *B01L 2200/147* (2013.01); *B01L 2300/0609* (2013.01); *B01L 2300/0627* (2013.01); *B01L 2300/0822* (2013.01); *B01L 2300/0867* (2013.01); *B01L 2300/0877* (2013.01); *B01L 2300/168* (2013.01); *B01L 2300/1822* (2013.01); *B01L 2400/0478* (2013.01)

(58) Field of Classification Search
  CPC ..... B01L 2300/0822; B01L 2300/0867; B01L 2300/0877; B01L 2300/168; B01L 2300/1822; B01L 2400/0478; B01L 3/502715; B01L 7/52; B01L 9/527; C12Q 1/6825; G01N 1/30; G01N 1/31; G01N 1/4022; G01N 33/5306
  See application file for complete search history.

(56) References Cited

U.S. PATENT DOCUMENTS

| | | | |
|---|---|---|---|
| 7,951,612 | B2 | 5/2011 | Angros et al. |
| 9,506,928 | B2 | 11/2016 | Eriksen et al. |
| 2002/0182653 | A1 | 12/2002 | Namimatsu |
| 2004/0029184 | A1 | 2/2004 | Gourevitch |
| 2006/0134793 | A1 | 6/2006 | Key et al. |
| 2010/0028978 | A1 | 2/2010 | Angros |
| 2010/0136612 | A1 | 6/2010 | Christensen et al. |
| 2012/0009666 | A1 | 1/2012 | Gerdes et al. |
| 2013/0071858 | A1 | 3/2013 | Bui et al. |
| 2013/0302818 | A1* | 11/2013 | Angros ............ G01N 35/00029 435/7.1 |
| 2014/0055853 | A1 | 2/2014 | Corwin et al. |
| 2015/0005190 | A1 | 1/2015 | Ciftlik et al. |
| 2015/0111202 | A1 | 4/2015 | Bui et al. |
| 2016/0312166 | A1 | 10/2016 | Lee et al. |

FOREIGN PATENT DOCUMENTS

| | | |
|---|---|---|
| JP | 2013-068612 A | 4/2013 |
| JP | 2015-517088 A | 6/2015 |
| WO | 2006/066039 | 6/2006 |
| WO | 2009/085574 | 7/2009 |
| WO | 2009/110936 | 9/2009 |
| WO | 2013/082612 A1 | 6/2013 |
| WO | 2013/128322 A1 | 9/2013 |

OTHER PUBLICATIONS

Ngyen et al "Microfluidics-assisted fluorescence in situ hybridization for advantageous human epidermal growth factor receptor 2 assessment in breast cancer" Nov. 2016Laboratory Investigation 97(1) DOI:10.1038/labinvest.2016.121 (Year: 2016).*
International Search Report and Written Opinion of the ISA for PCT/EP2018/068830 dated Oct. 9, 2018, 13 pages.
Ciftlik et al., "Microfluidic processor allows rapid HER2 immunohistochemistry of breast carcinomas and significantly reduces ambiguous (2+) read-outs," PNAS, vol. 110, No. 14, Apr. 2, 2013, 16 pages.
D'Andrea et al., "Application of triple immunohistochemistry to characterize amyloid plaque-associated inflammation in brains with Alzheimer's disease", Biotechnic & Histochemistry 2001, vol. 76(2), pp. 97-106.
Long II et al., "Microwave oven-based technique for immunofluorescent staining of paraffin-embedded tissues", J Mol Histol., vol. 39(1), Feb. 2008, 7 pages.
McMahon et al., "The use of microwave irradiation as a pretreatment to in situ hybridization for the detection of measles virus and chicken anaemia virus in formalin-fixed paraffin-embedded tissue," Histochemical Journal, vol. 28, 1996, pp. 157-164.
Shi et al., "Antigen Retrieval in Formalin-fixed, Paraffin-embedded Tissues: An Enhancement Method for Immunohistochemical Staining Based on Microwave Oven Heating of Tissue Sections," The Journal of Histochemistry and Cytochemistry, vol. 39, No. 6, 1991, pp. 741-748.
Temel et al., "A simple and rapid microwave-assisted hematoxylin and eosin staining method using 1, 1, 1 trichloroethane as a dewaxing and a clearing agent," Biotechnic & Histochemistry 2005, vol. 80(3-4), Mar. 24, 2005, pp. 123-132.
Werner et al., "Antigen retrieval, signal amplification and intensification in immunohistochemistry," Histochem Cell Biol (1996), vol. 105, pp. 253-260.
S. Yamashita, "Heat-induced antigen retrieval: Mechanisms and application to histochemistry," ScienceDirect—Progress in Histochemistry and Cytochemistry, vol. 41, 2007, pp. 141-200.

* cited by examiner

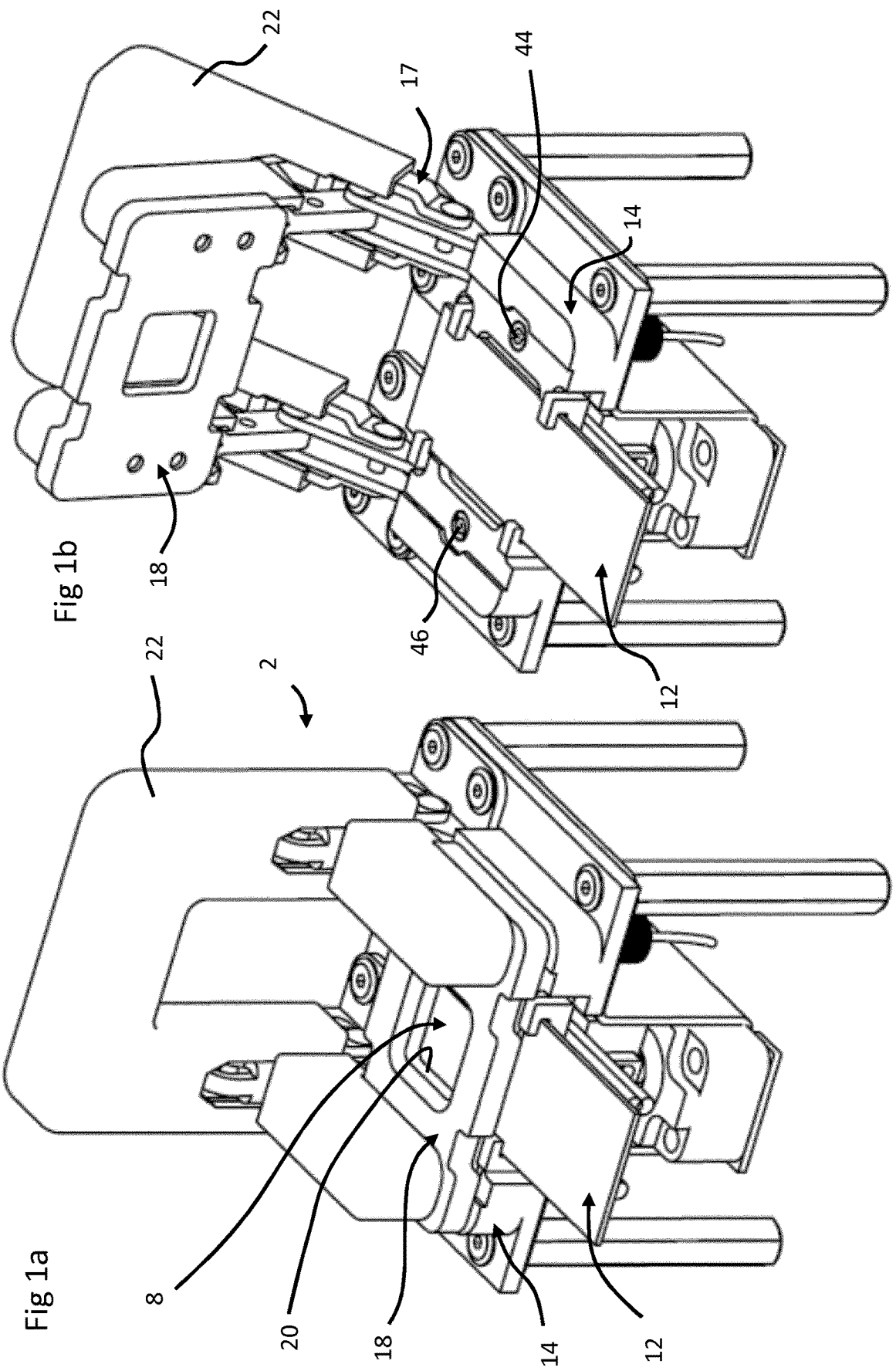

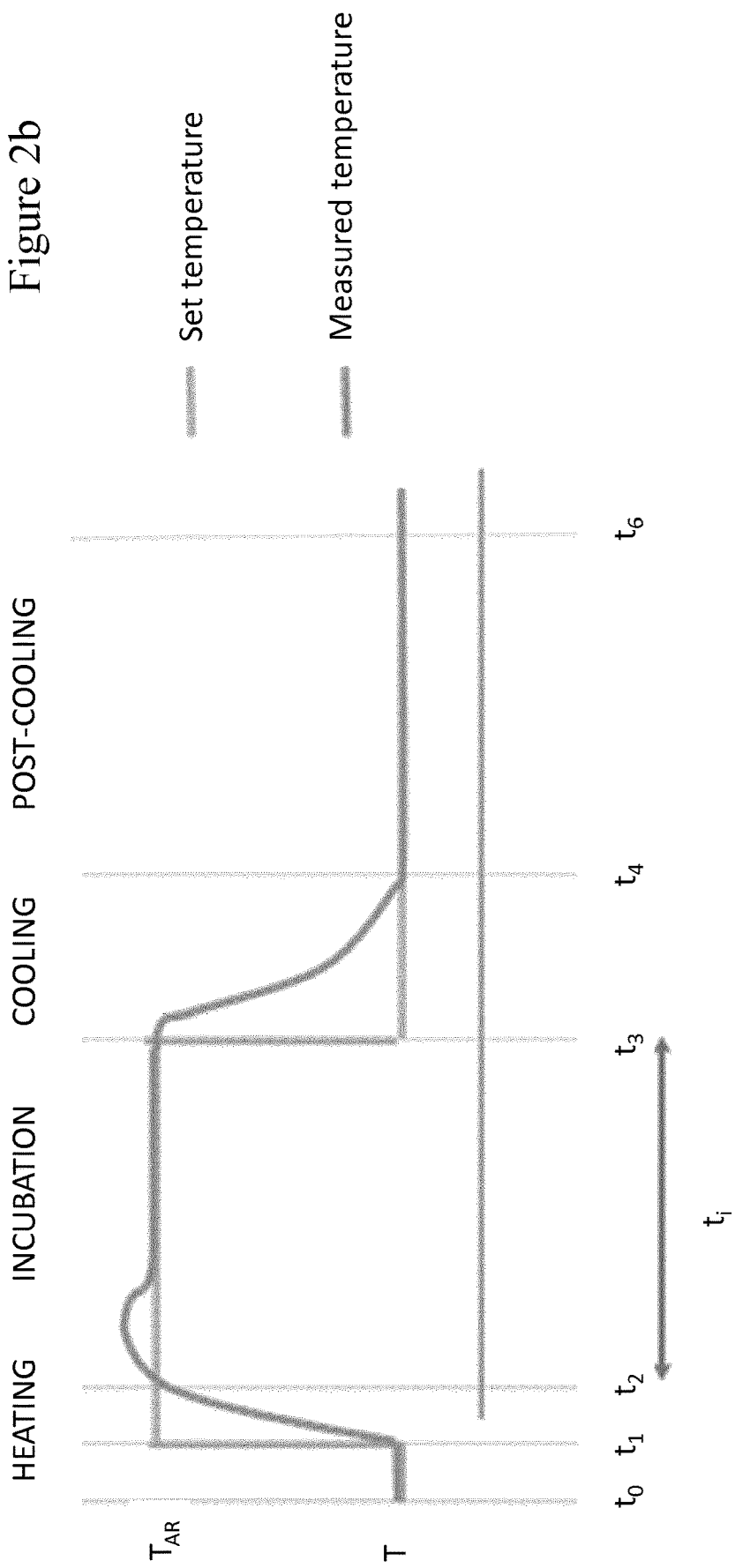

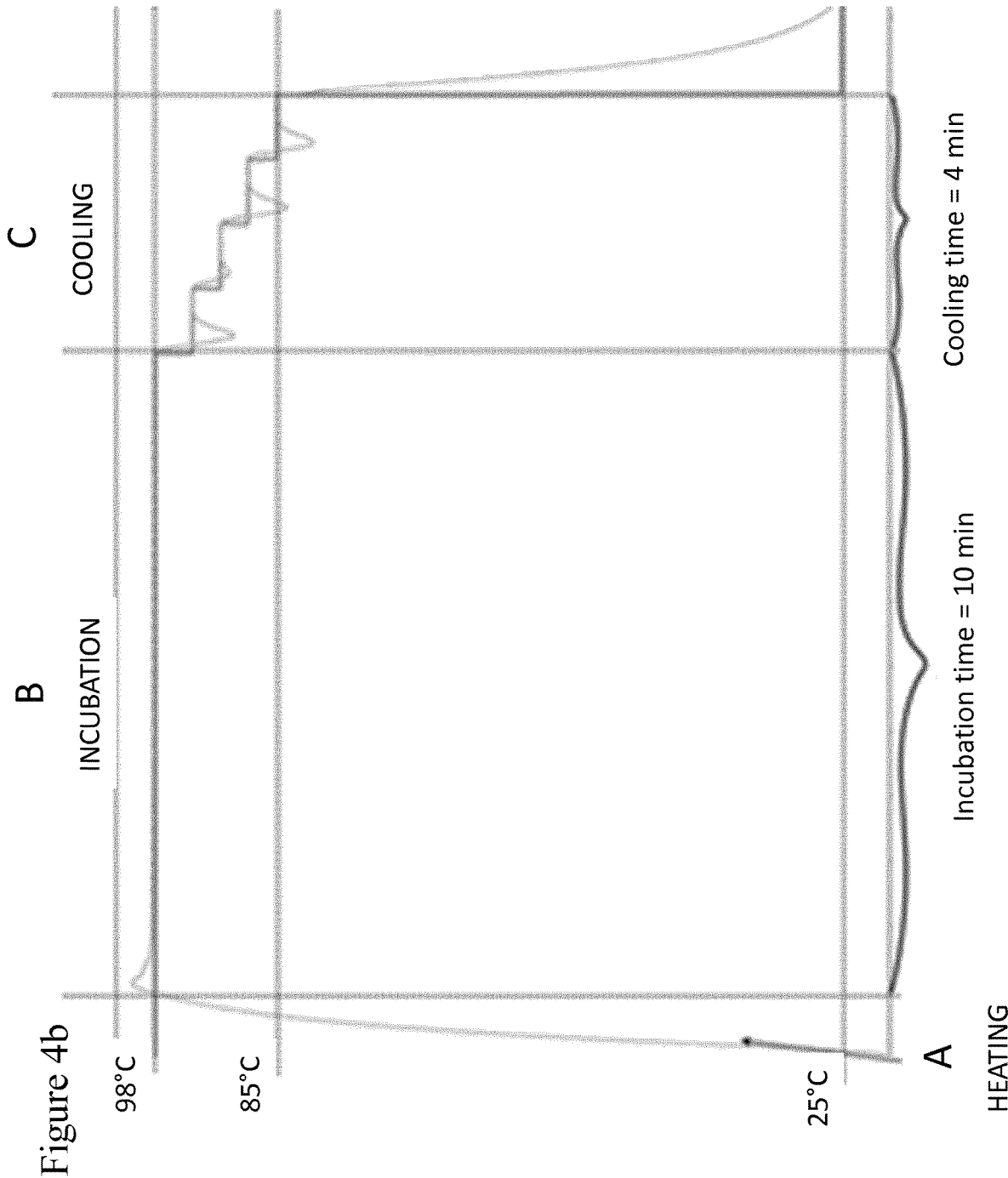

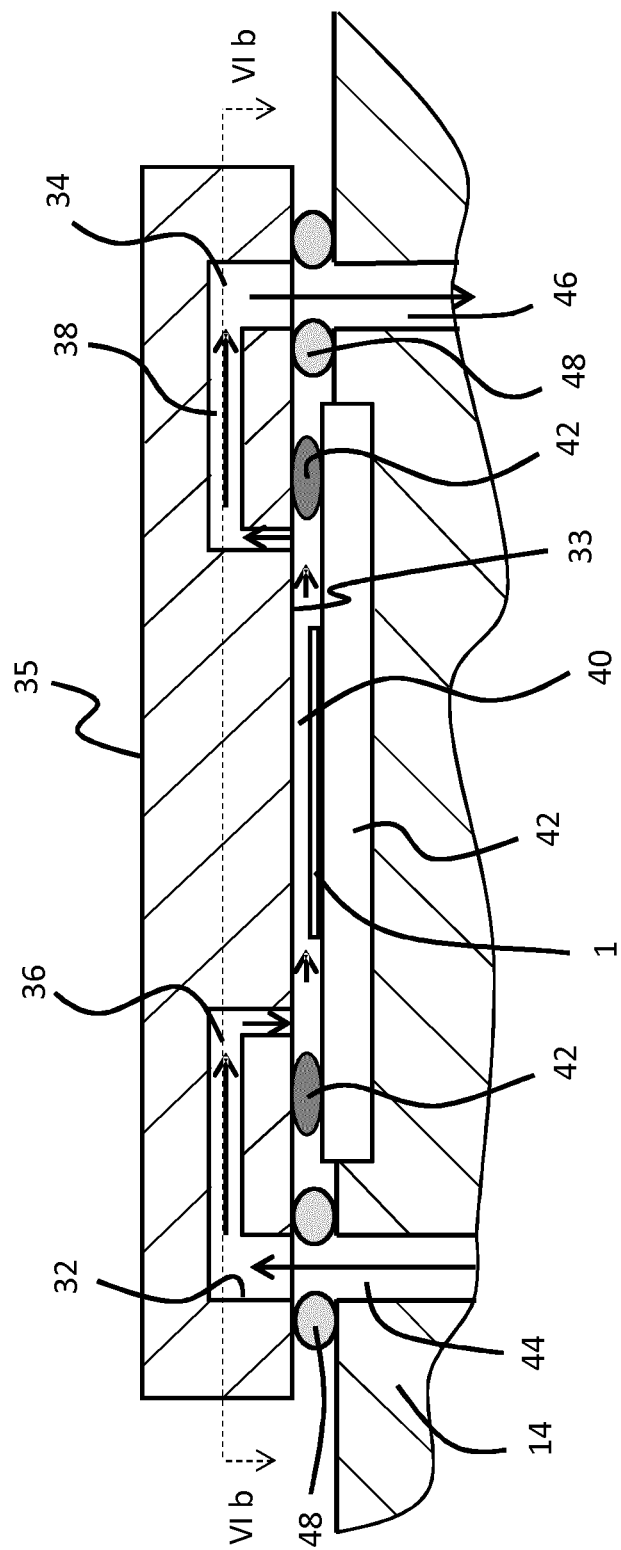

METHODS OF IN SITU ANTIGEN RETRIEVAL OF A BIOLOGICAL SAMPLE AND IMAGING THEREOF

This application is the U.S. national phase of International Application No. PCT/EP2018/068830 filed Jul. 11, 2018 which designated the U.S. and claims priority to EP Patent Application No. 17180896.7 filed Jul. 12, 2017, the entire contents of each of which are hereby incorporated by reference.

FIELD OF THE INVENTION

The present invention pertains generally to the fields of biological sample preparation, in particular antigen retrieval in view of in situ imaging of samples.

BACKGROUND OF THE INVENTION

Immunohistochemistry (IHC) is a technique involving the use of specific probe molecules such as antibodies to detect the existence of specific biomarkers (e.g. antigens) that may be expressed by cells in a tissue sample. IHC is widely used in both clinical and research settings, for example to diagnose particular diseases such as a type of cancer or to investigate the correlation between disease prognosis and the expression of novel biomarkers. The dominant application area of IHC is cancer diagnosis; but it has other application areas including the detection of infectious agents such as viruses (McMahon et al., 1996, *Histochem J.*, 28(3):157-64) and aiding the diagnosis of other diseases such as Alzheimer's (Dandrea et al., 2001, *Biotech Histochem.*, 76(2):97-106).

Antigen retrieval (AR) is a pre-processing technique for IHC that is used to increase the antigenicity of various types of tissue samples, predominantly formalin-fixed paraffin embedded (FFPE) tissue sections. It has been rapidly adapted as an industry gold standard for a wide range of tissue types and target markers since its initial introduction (Shi et al., 1991, *J Histochem Cytochem.*, 39:741-748; U.S. Pat. No. 5,244,787).

While the exact mechanism behind the efficacy of the antigen retrieval process is still unclear, there is consensus on its effect of reversing the formation of formalin-induced peptide bonds to activate the target epitopes. There are two main methods used for increasing the responsivity of epitopes: Enzyme-induced antigen retrieval (EIAR) and heat-induced antigen retrieval (HIAR). Because of the inherently catalytic nature of enzymatic substances, EIAR has a higher potential to disturb the tissue morphology and render the target protein sites non-functional (Werner et al., 1996, *Histochemistry and Cell Biology*, 105:4 253-260). Therefore, HIAR is the more widely used method among the two.

There are different apparatus and methodologies for performing HIAR. A conventional method is the incubation of samples in a hot bath containing basic buffers. For this method, as a general trend, a longer incubation time is required to obtain the same antigenicity for lower AR temperatures. For example, an overnight incubation at 60° C. or a 1-hour incubation at 95° C. have both been reported to be used successfully for pre-IHC AR (Yamashita, 2007, *Prog Histochem Cytochem.*, 41(3):141-2007). Microwave treatment is another popular method where the sample undergoes either a constant-power microwave treatment or heat-and-pause cycles (U.S. Pat. No. 5,244,787). It is also used to improve antigenicity in immunofluorescence (Long and C. Buggs, 2008, *J Mol Histol.* 39(1): 1-4) and special staining applications (Temel et al., 2005, *Biotech Histochem.* 80(3-4):123-32).

It is also possible to combine HIAR and EIAR methods. Key et al. disclosed AR buffers containing heat-stable enzymes which are used in microwave treatment of FFPE samples. Successful AR for various breast cancer markers were shown with these methods where the AR temperature goes up to 100° C. (WO 2009/110936). Another alternative is pressure-assisted HIAR where it becomes possible to increase the temperature of the AR medium beyond its atmospheric boiling temperature. Angros et al. disclosed an automated apparatus for performing AR in high-pressure environments for this purpose (U.S. Pat. No. 7,951,612).

HIAR can be performed in different environments or in different solutions modified to improve AR performance. For example, Gourevitch disclosed novel solutions to promote sample integrity during AR (US 2004/0029184) and Namimatsu disclosed the use of AR solutions containing CCA and NaOH to enhance AR performance (US 2002/0182653). Eriksen disclosed AR solutions spiked with various nonionic surfactants for the reversal of specific cross-links between amine groups present in the target epitopes (U.S. Pat. No. 9,506,928).

A large number of AR solution formulations are known in the art to increase the boiling point of the solution at atmospheric pressure so that AR can be performed at an elevated temperature. Key et al. disclosed AR solutions with different additives and viscosities for boiling points increased to up to 135° C. in addition to apparatus for automated sample temperature control (US 2006/0134793, WO 2009/085574). Christensen et al. disclosed a horizontal AR apparatus and methods where an AR temperature of 120° C. to 130° C. was obtained with the use of modified buffers (US 2010/0136612). Kram et al. disclosed AR solutions comprising organic salts or ionic liquids to reach boiling points in excess of 200° C. (WO 2006/066039).

The successive application of different buffers to improve AR efficiency is also known in the art. For example, Gerdes et al. discloses methods of treating a sample with AR buffers with different pH values for the detection of multiple antigens (US 2012/009666).

Another approach for decreasing the sample pre-processing time before immunostaining is providing buffers which are used in both deparaffinization and antigen retrieval of FFPE samples. Aghassi et al. disclosed buffers containing various surfactants which were used for simultaneous deparaffinization and AR (U.S. Pat. No. 6,649,368).

The above-mentioned methods inadequately address the issues of high sample processing time and low efficiency, in particular because antigen retrieval is performed as part of the sample preparation, before the staining process.

Therefore, there is a need for new techniques, instrumentation and tools for performing tissue processing methods requiring reduced processing time since a reduction in process times translates to a higher throughput in the pathologic workflow and a more efficient use of limited clinical laboratory resources.

SUMMARY OF THE INVENTION

An object of this invention is to provide a method of in situ temperature-induced antigen retrieval of samples wherein all steps are performed under a pressure higher than the atmospheric pressure on a sample immobilized on a sample support allowing the antigen retrieval before staining and imaging said sample on the same sample support.

It is advantageous to provide a method of in situ temperature-induced antigen retrieval of samples under a pressure higher than the atmospheric pressure that enables to achieve a fully automated and quick high-temperature induced denaturation effect and cooling-induced refolding temperature which allows a rapid and reproducible temperature-induced unmasking of target epitopes.

It is advantageous to provide a method of in situ temperature-induced antigen retrieval of tissue or cell samples immobilized on a sample support that allows subsequent staining and imaging of said sample on the same sample support where the sample integrity is maintained and the process time is decreased by the avoidance of subjecting the sample to multiple handling steps for antigen retrieval before staining and mounting the sample on various sample supports for antigen retrieval and staining.

In another mode of implementation, it is advantageous to provide a method of in situ temperature-induced antigen retrieval of tissue or cell samples immobilized on a sample support and subject said sample to subsequent staining and imaging on the same sample support, where the temperature of the sample after the temperature-induced antigen retrieval step is cooled to a temperature higher than the room temperature and the subsequent staining and imaging steps are conducted at a temperature higher than the room temperature, decreasing the process time and increasing the efficiency of the staining.

In another mode of implementation, it is advantageous to provide a method of in situ temperature-induced antigen retrieval of tissue or cell samples immobilized on a sample support wherein the said sample is subjected on the same sample support to a subsequent fully controllable flow of imaging probe(s) directly at the surface of the sample in a specific sequence for carrying out a complete cycle of sample labelling and imaging and repeating such cycle in a high-throughput manner which facilitates immunostaining of different markers on the same sample and increases the number of possible sample labeling cycles without degradation of reproducibility and/or sensitivity of the measured imaging signal.

Objects of this invention have been achieved by providing a method according to claim 1.

Disclosed herein, according to a first aspect of the invention, is a method for in situ temperature-induced antigen retrieval of a biological sample immobilized on a sample support, comprising the steps of:
a) providing said biological sample immobilized on said sample support;
b) providing a microfluidic device comprising a microfluidic chamber, at least one fluid inlet at one end of said microfluidic chamber and at least one fluid outlet at another end of said microfluidic chamber configured to conduct a fluid supplied under pressure from a fluid feeding system through the microfluidic chamber, wherein at least one wall of the microfluidic chamber is formed by the sample support and is mounted against a seal in a fluid-tight and removable manner to a first wall of the microfluidic chamber by a clamping mechanism and wherein the volume of the microfluidic chamber is between 2.5 µL and 200 µl;
c) mounting said microfluidic chamber and said sample support together in a fluid-tight manner with the sample facing an inside of the microfluidic chamber;
d) carrying out a temperature-controlled antigen retrieval step at a pressure higher than the atmospheric pressure, wherein said retrieval step comprises:

filling the micro fluidic chamber with an epitope unmasking solution through the fluid inlet at a pressure $P_{chamber}$ in the microfluidic chamber above atmospheric pressure heating the microfluidic chamber to an incubation temperature setpoint ($T_{AR}$) and maintaining the temperature of the microfluidic chamber to said incubation temperature setpoint for an incubation period duration $t_i$;

cooling the microfluidic chamber to a cooling temperature below the said incubation temperature setpoint and higher or equal to room temperature for a cooling period duration $t_c$, wherein said incubation temperature setpoint $T_{AR}$ is comprised between about 60° C. to 200° C., pressure $P_{chamber}$ in the microfluidic chamber is greater than 1.5 bars, wherein the incubation period duration $t_i$ is comprised between 0.5 to 30 min.

In an advantageous embodiment, T the cooling period duration $t_c$ may be comprised between 1 to 30 min.

In an advantageous embodiment, the incubation temperature setpoint $T_{AR}$ during the temperature-controlled antigen retrieval step S1 may be comprised between 110° C. and 200° C.

In an advantageous embodiment, the pressure $P_{chamber}$ in the microfluidic chamber during the temperature-controlled antigen retrieval step S1 may be comprised between about 2.5 to 5 bars.

In an advantageous embodiment, the incubation period duration $t_1$ may be comprised between 2 to 20 min, preferably between 2 to 15 min.

In an advantageous embodiment, the method of the invention further comprises the steps of:
e) injecting in sequence a plurality of reagents, including at least one imaging probe, through the fluid inlet into the microfluidic chamber, at a flow rate in a range between about 1 µl/s and about 100 µl/s;
f) imaging a signal emitted by components of the sample reacted with said at least one imaging probe;
g) repeating steps (e) and (f) with different imaging probes.

In an advantageous embodiment, the injecting in sequence a plurality of reagents includes:
an elution step where an elution buffer is injected for removing undesirable material potentially remaining on the sample;
an optional non-specific binding blocking step where a blocking buffer is injected;
a sample labelling step where an imaging probe is injected; and
wherein each of these steps may be preceded by an optional washing step wherein a washing buffer is injected, wherein said at least one imaging probe results from the injection of a sequence of specific antibodies as labelling probes and chromogen or fluorescent detection molecules, targeting the molecular entities to be analyzed within the said sample.

In an advantageous embodiment, each step in the sequence of injected plurality of reagents comprises for each reagent two flow rate steps:
a first flow rate step where the reagent is injected at an initial flow rate in a range between about 1 µl/s and about 100 µl/s;
a second flow rate step where the same reagent is injected at a lower flow (typically from about 0.001 to about 1.0 µl/s) to ensure incubating said reagent with the sample, before injecting the next reagent in the sequence.

In an advantageous embodiment, the first flow rate step lasts between 1 s and 120 s.

In an advantageous embodiment, the second flow rate step of a reagent lasts from about 1 min to about 30 min.

In an advantageous embodiment, the sample labeling step may comprise injecting at least one labeled probe such for in-situ hybridization with some DNA/RNA material within the sample, such as a labeled RNA or DNA probe.

In an advantageous embodiment, the sample labeling step may further comprise applying temperature cycles within the microfluidic chamber for hybridizing DNA/RNA material within the sample with the RNA or DNA probes.

In an advantageous embodiment, the imaging step may be conducted by fluorescence microscopy or bright field microscopy.

In an advantageous embodiment, the elution step may be carried out while applying a temperature cycle for ensuring removal of undesirable in-situ hybridized probes or markers potentially remaining on the sample before repeating the method with another sample labelling step.

Other objects of this invention have been achieved by providing a device according to claim 7.

Disclosed herein, according to a second aspect of the invention, is a biological sample processing device suitable for use in a method according to any of the preceding claims, comprising a support mechanism, a thermal unit, a microfluidic device, a pressurized fluid feeding system, and a control system, the microfluidic device comprising a micro fluidic chamber having a volume comprised between 2.5 μL and 200 μl, at least one fluid inlet at one end of said microfluidic chamber and at least one fluid outlet at another end of said microfluidic chamber configured to conduct a fluid through the micro fluidic chamber for reaction with the sample inside said microfluidic chamber, at least one wall of the microfluidic chamber is formed by the sample support and is mounted against a seal in a fluid-tight and removable manner to a first wall of the microfluidic chamber by a clamping mechanism configured to compressed the seal between the sample support and microfluidic device to an extent sufficient to contain a pressure $P_{chamber}$ in the microfluidic chamber greater than 1.5 bars, preferably greater than 2 bars, in particular greater than 2.5 bars, more preferably greater than 3 bars.

In an advantageous embodiment, the microfluidic device may be in the form of a substantially flat substrate of light-transparent material comprising therein a microfluidic inlet channel network connected to a fluid inlet orifice, and a micro fluidic outlet channel network connected to a fluid outlet orifice, both the fluid inlet orifice and fluid outlet orifice opening onto a first side of the substrate corresponding to a chamber bounding side of the substrate.

In an advantageous embodiment, a height of the chamber between the first face and sample support is less than 100 μm configured to ensure advective transport of the reagent along the biological tissue sample placed on the sample support.

In an advantageous embodiment, the support mechanism comprises a base structure and said clamping mechanism, the clamping mechanism comprising a clamping plate provided with a window to allow viewing of the biological sample through the transparent substrate with a microscope.

In an advantageous embodiment, the microfluidic device may be positioned on top of the sample support with a chamber side of the microfluidic device and seal facing down against the sample support and over the biological sample.

In an advantageous embodiment, the fluid feeding system under pressure comprises a fluid supply channel and a fluid exit channel mounted in the base structure, each comprising seals at their orifice ends facing a movable clamping plate of the clamping mechanism, the seals being compressed against a chamber facing side of a substrate of the microfluidic device at a position around the fluid inlet orifice, respectively fluid outlet orifice of the microfluidic device, said seals under compression being configured to support a pressure of at least 1.5 bars, preferably greater than 2 bars, in particular greater than 2.5 bars, more preferably greater than 3 bars.

In an advantageous embodiment, the thermal unit is mounted in the base structure below a position of the sample support, the thermal unit comprising a heating unit, optionally mounted in a heat transfer unit that conducts heat to the sample support and that is positioned just below the sample support.

In an advantageous embodiment, the heating unit comprises a Peltier device or a plurality of stacked Peltier devices.

In an advantageous embodiment, the thermal unit further comprises a cooling unit, for instance in the form of a cooling block comprising a labyrinth of fluid flow channels for a cooling fluid to flow therethrough to provide active cooling of the sample support.

In an embodiment, the sample processing device further comprises one or a plurality of temperature sensors integrated in the base structure and/or clamping plate configured to measure the temperature in the sample support or the microfluidic device and/or in the heating unit and/or heat transfer unit, the one or more temperature sensors forming part of a temperature control system configured to control operation of the thermal unit.

BRIEF DESCRIPTION OF THE DRAWINGS

FIG. 1a illustrates a biological sample processing device 2 according to an embodiment of the invention, the device shown in a closed position ready for use;

FIG. 1b is a perspective view of the device of FIG. 1a showing a clamping mechanism in an open position, with a microfluidic network device removed;

FIG. 1c is a cross-sectional view along line 1c-1c of FIG. 1a;

FIG. 1e is a cross-sectional view through line 1e-1e of FIG. 1a;

FIG. 6a is a schematic cross-sectional view of a micro fluidic device and sample support of the biological processing device according to an embodiment of the invention.

DETAILED DESCRIPTION OF THE INVENTION

Figure 1D:
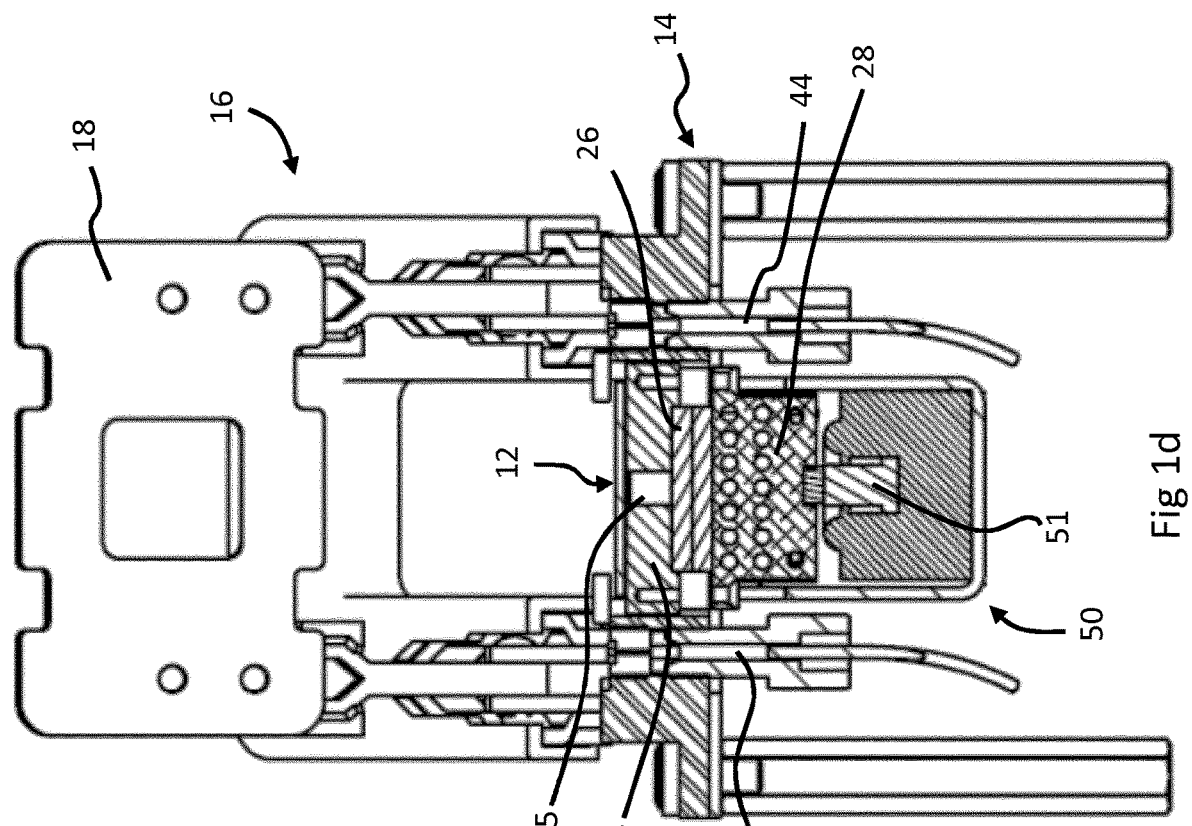
FIG. 1d is a cross-sectional view along line 1d-1d of FIG. 1b.
Figure 1C:
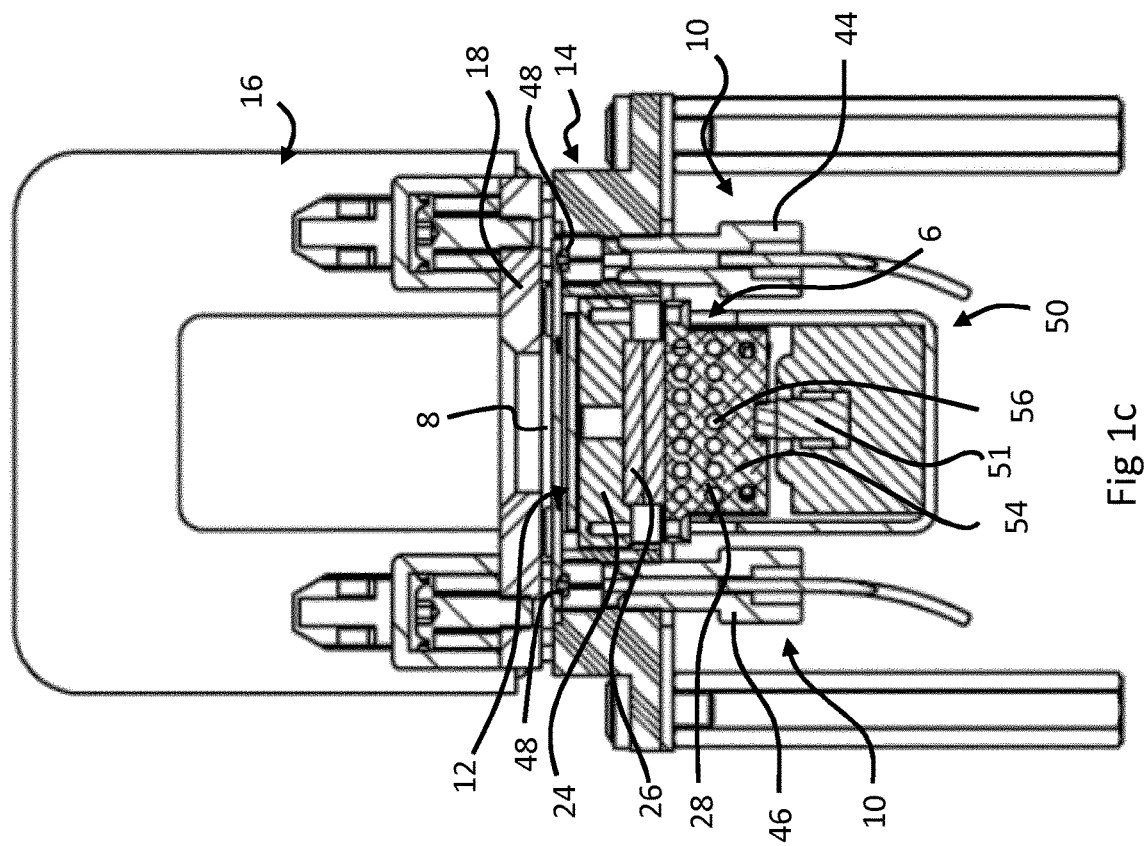

The expression "epitope unmasking solution" refers to any solution that is suitable for heat-induced epitope retrieval and which is known to the skilled person. Typical epitope unmasking solutions are those as described in "*Microscopy, Immunohistochemistry, and Antigen Retrieval Methods: For Light and Electron Microscopy*" by M. A. Hayat, 2002, Springer Science+Business Media New York Referring to the figures, in particular first to FIGS. 1a-1g and 6a-6b, a biological sample processing device 2 according to an embodiment of the invention is illustrated. The biological sample processing device 2 is configured for conducting in situ temperature-induced antigen retrieval of biological samples, and may be further configured to perform in situ imaging of samples by cycle multiplexing. The biological sample processing device 2 is configured to inject reagents in a microfluidic chamber 40 at a pressure higher than atmospheric pressure in order to heat reagents injected in the chamber 40 at a temperature at or exceeding boiling temperature of the reagent at atmospheric pressure. In an advantageous embodiment, the device is configured for a pressure in the chamber in a range of 1.5 to 5 bars.

In an embodiment of the invention, the sample processing device 2 comprises a support mechanism 4, a thermal unit 6, a microfluidic device 8, a pressurized fluid feeding system 10, and a control system (not shown).

The control system comprises a microprocessor that receives temperature and pressure inputs from temperature and pressure sensors of the device 2, for automatic or user-based control of the thermal unit and pressurized fluid feeding system, for controlling the temperature and fluid pressure parameters of the device, in particular of the fluids and reagents injected into the microfluidic chamber 40.

The sample processing device 2 receives a biological sample support 12 therein. The biological sample support may for instance be in the form of a glass slide for visioning under a microscope, as per se commonly known for the microscopic inspection of tissue samples and other biological samples.

The microfluidic device 8 is, in a closed position, mounted against the sample support 12 as best seen in FIG. 6a and forms therebetween a microfluidic chamber 40. The microfluidic device comprises a seal 42 that is configured to completely surround the chamber 40 whereby when the sample support 12 is clamped against the microfluidic device 8 under a certain clamping force F the seal 42 is compressed between the sample support 12 and microfluidic device 8 to an extent sufficient to withstand at least over 1.5 bars of pressure, and in embodiments, up to 5 bars or more. The reagent injected in the chamber 40 can thus be supplied under a pressure in the range of 1.5 to 5 bars or more during the antigen retrieval process in order to be able to heat the reagent at temperatures exceeding boiling point at atmospheric pressure.

The microfluidic device 8, in an embodiment, is in the form of a substantially flat substrate 9 of light-transparent material. The substrate comprises therein a microfluidic inlet channel network 36 connected to a fluid inlet orifice 32, and a micro fluidic outlet channel network 38 connected to a fluid outlet orifice 34. Both the fluid inlet orifice 32 and fluid outlet orifice 34 open onto a first side 33 of the plate corresponding to a chamber bounding side of the substrate 9.

The micro fluidic inlet channel network 36 feeds into a plurality of orifices 37 extending along an inlet edge of the chamber 40 where the reagents flow into the chamber. The microfluidic outlet channel network 38 feeds into a plurality of orifices 39 extending along an outlet edge of the chamber 40 where the reagents flow out of the chamber. The microfluidic inlet and outlet channel networks 36, 38 are formed within the substrate and configured to interconnect the single inlet 32 to the plurality of chamber inlet orifices 37, respectively the single outlet to the plurality of chamber outlet orifices 39.

According to one particular aspect, the micro fluid chamber 40 is configured for advective transport of fluids inside said microfluidic chamber 40. The height of the chamber between the first face 33 and sample support 12 is preferably less than 100 μm in order to enable and ensure advective transport of the reagent along the biological tissue sample 1 placed on the sample support. Advective transport provides an optimal exchange between the reagent and the tissue sample. The low chamber height also ensures a minimal volume within the chamber 40 that allow it to be heated very quickly, and if needed, to be cooled quickly or at a desired controlled rate of cooling, thus reducing the time for antigen retrieval at high temperatures.

The seal 42 may be in the form of a gasket seal that is partially embedded in a corresponding groove in the substrate 9 surrounding the chamber 40, chamber inlet orifices 37 and chamber outlet orifices 39.

Figure 1F:
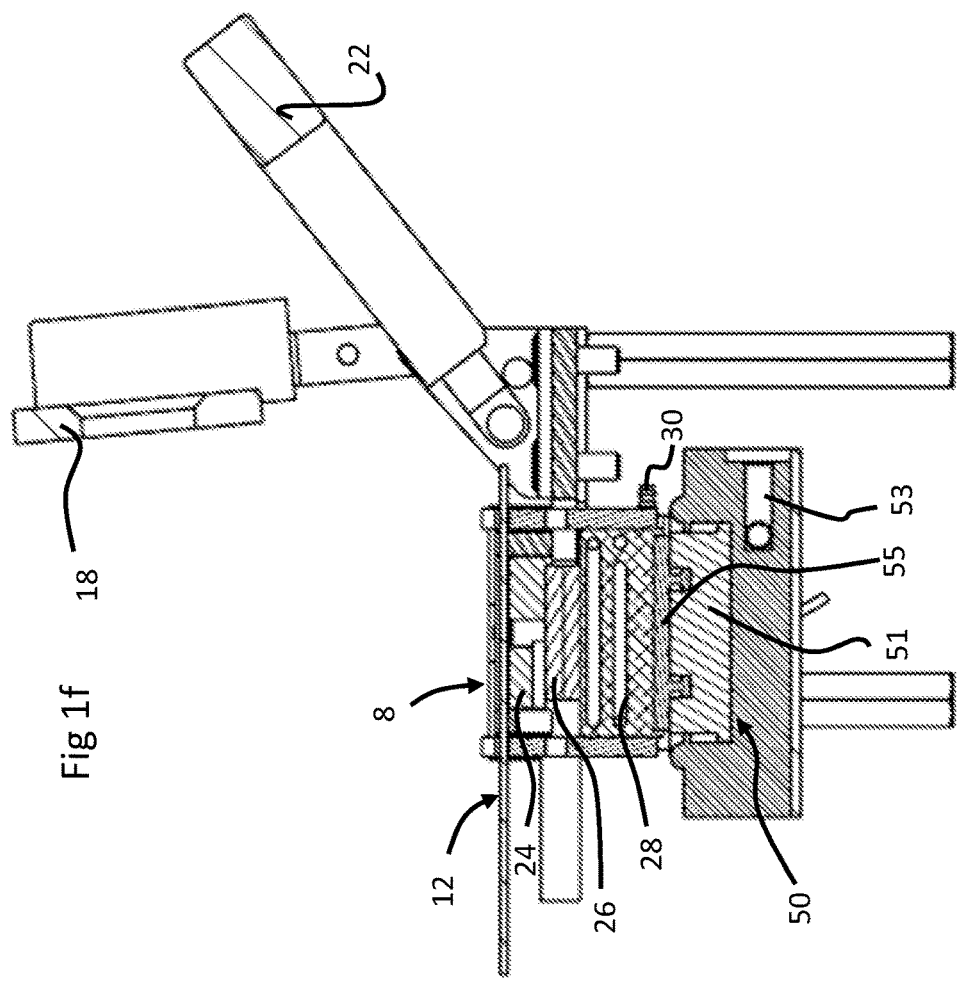
FIG. 1f is a cross-sectional view through line 1f-1f of FIG. 1b.
Figure 1E:
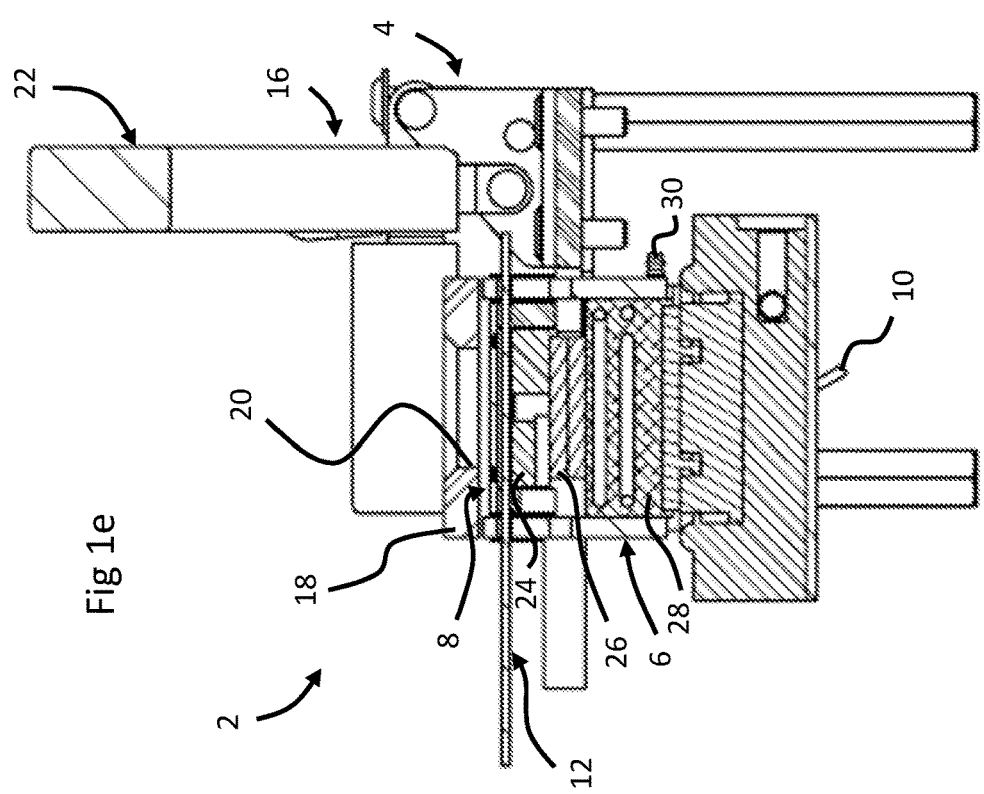

The support mechanism 4 comprises a base structure 14 and a clamping mechanism 16, the clamping mechanism comprising a clamping plate 18 actuated by an actuation lever mechanism 22. As shown in FIGS. 1d and 1f, the clamping plate 18 is in an up and open position. The sample support 12 can be positioned on the base 14 with the biological sample 1 facing upwards. The microfluidic device 8 may be positioned on top of the sample support 12 with the chamber side 33 and seal 42 facing down against the sample support 12 and over the biological sample. A window 20 may be provided in the clamping plate 18 in order to allow viewing of the biological sample 1 through the transparent substrate 9 with a microscope. A spacer plate 19, for instance in a transparent polymer or glass may be provided on a bottom of the clamping plate to act as an interface between the clamping plate 18 and the microfluidic device 12.

The fluid feeding system under pressure 10 comprises a fluid supply channel 44 and a fluid exit channel 46 both the fluid supply and outlet channels comprising seals 48 at their orifice ends facing the clamping plate 18. The seals 48 may for instance be in the form of small gaskets or O-rings that fit partially into a corresponding groove in the base 14. When the device is closed, the seals are compressed against the chamber facing side 33 of the substrate 9 at a position around the fluid inlet orifice 32, respectively fluid outlet orifice 34 of the microfluidic device 8. Thus, when the microfluidic device is placed on top of the sample support 12 the seal 42 of the microfluidic device are compressed against the sample support 12 and the seals 48 of the fluid feeding system are compressed between the substrate 9 and the base 14. The compression and sealing arrangement is configured to support a pressure of at least 1.5 bars, preferably in a range of 2 to 5 bars or more.

The clamping mechanism 16 has a hinge linkage 17 with a lever arm effect that allows a high clamping force, for instance in the range of 30 Newtons to 500 Newtons, to be applied on the substrate 9 of the microfluidic network device 8. Articulated mechanisms used in various arts that may provide such effects are per se well-known and need not be described in more detail. Within the scope of the invention, various clamping means configured to produce the required forces for clamping the microfluidic device down against the base and sample support may be used.

Figure 1G:
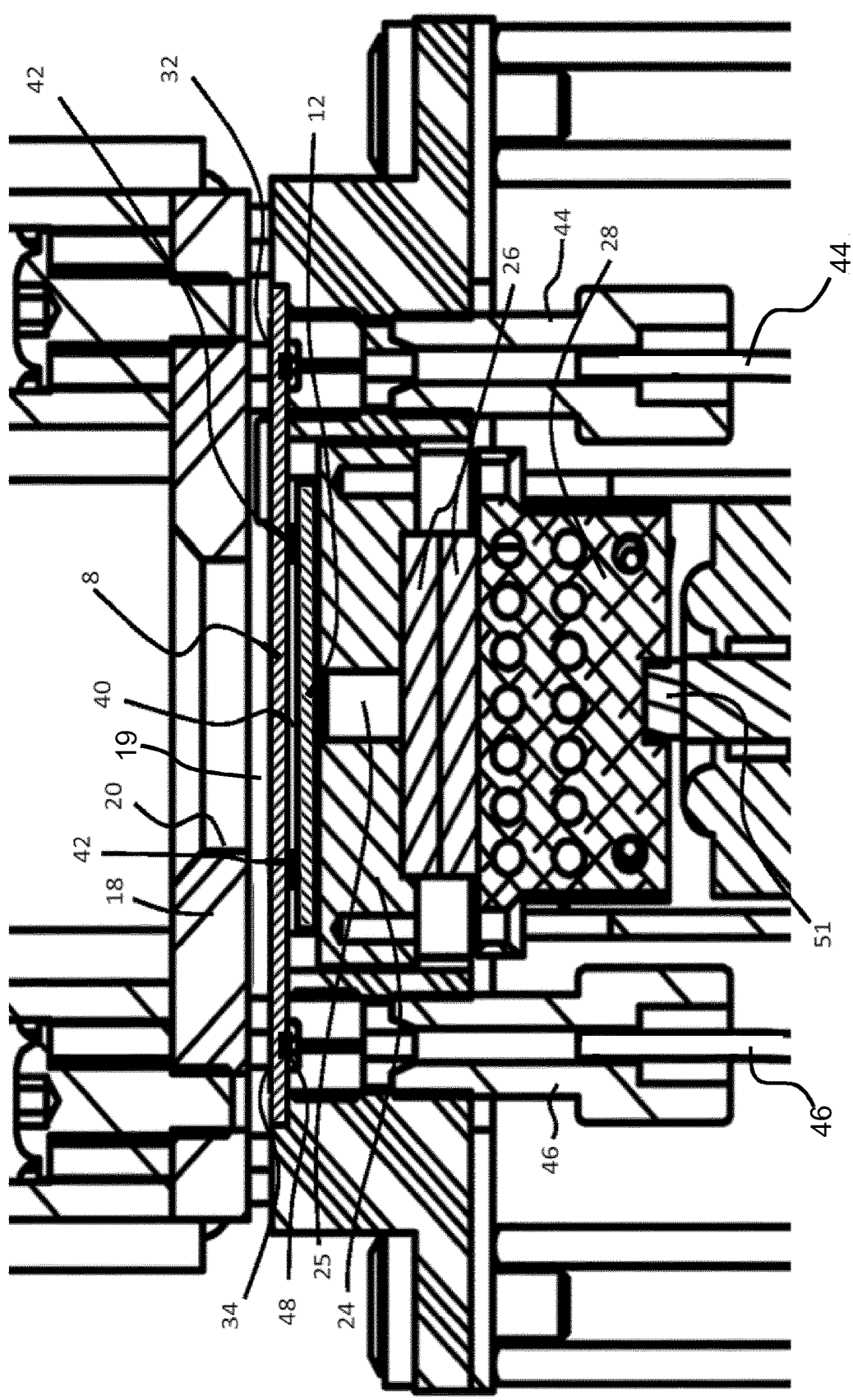
FIG. 1g is an enlarged view of part of the cross-section view of FIG. 1c.

The fluid inlets and outlets 44, 46 may be connected to an underside of the base structure 14 as best illustrated in FIG. 1g and connected to tubes connected to a fluid supply and disposal system (not shown). The fluid supply and disposal system comprises a pump system connected to supplies of the required reagents, the pump system configured to deliver the reagent to the biological sample processing device 2 at pressures exceeding 1.5 bars, preferably exceeding a pressure in a range of 2-5 bars or more.

The thermal unit 6 is mounted in the base structure 14 below the position of the sample support 12. The thermal unit comprises a heating unit 26 which may advantageously comprise a Peltier device or a plurality of Peltier devices, for example a pair of stacked Peltier devices 1. The heating unit 26 however may also in variants comprise other heater devices such as an induction coil or a resistive electrical heater. The heating unit 26 may, as shown in the illustrated embodiment, optionally be mounted in a heat transfer unit 24 that conducts heat to the sample support 12 and that is positioned just below the sample support 12. The heating unit 26 or heat transfer unit 24 may either be in direct contact against the sample support 12, or be separated therefrom with a small gap. In the illustrated embodiment, the Peltier devices 26 are mounted in the heat transfer unit 24 that forms essentially a conductive block, for instance made of a metal to conduct heat to the sample support 12. A passage 25, or a plurality of passages may be provided in the heat transfer unit 24 between the heating unit 26 and the sample support 12 for heat transfer by conduction and radiation. The passage 25 may also serve, alternatively or in addition, to mount a temperature sensor therein of a temperature control system, for controlling operation of the thermal unit 6, and in particular the operation of the heating unit 26.

The thermal unit 6 may optionally further comprises a cooling unit 28, for instance in the form of a cooling block 54 comprising a labyrinth of fluid flow channels 56 for a cooling fluid to flow therethrough in order to provide active cooling of the sample support 12 at the end of the antigen retrieval step under high temperature. Depending on the variant however, an active cooling may not be required, and a passive cooling could be implemented, for instance by omission of the cooling unit 28 or by air cooling of the cooling unit 28 without a cooling fluid passing within the cooling unit block. The thermal unit may be clamped to the base 14 by a fixed mounting structure, or by means of a clamping device 50.

The clamping device may advantageously be provided with an adjustable piston mechanism 51. The piston mechanism may be mechanically or hydraulically or pneumatically actuated. In a preferred embodiment, the piston mechanism is actuated by compressed gas, for instance compressed air, injected under the piston 51 through an inlet 53. The piston mechanism 51 serves to push the sample support 12 from below against the microfluidic device 8 to improve clamping and fluidic sealing with the seal 42 compressed between the microfluidic device 8 and sample support 12 and allows to automatically compensate for any misalignment/non-flatness between the sample support 12 and the microfluidic device 8, preventing leakage under the high-pressures (typically over 3 bars) that may be implemented in the present invention. The piston mechanism may also serve to adjust the pressure of the cooling unit against the heating unit 26 and base 14. The compressed gas actuation of the piston mechanism advantageously provides a stable and accurately controlled biasing force of the sample support 12 against the microfluidic device 8.

The biological sample processing device 2 may further comprise one or a plurality of temperature sensors integrated in the base structure 14 (e.g. in the passage 25) and/or clamping plate 18 configured to measure the temperature in the sample support 12 or the microfluidic device 8, and/or in the heating unit 26 and/or heat transfer unit 24. The temperature sensor may comprise various sensors per se well known in the art of temperature measurement, for instance by optical detectors, infrared detectors. In a preferred embodiment, the temperature sensor is a resistive sensor. A temperature sensor may also be connected to the fluid outlet 44. The one or more temperature sensors may form part of a temperature control system configured to control, inter alia, operation of the thermal unit during antigen retrieval processing steps.

In an embodiment, the temperature control system as well as the thermal unit 6 are connected to an automated control system. The control system can comprise any useful combination of feedback elements known in the art, e.g. proportional, integral and derivative feedback elements to control the pump and valve system for supply of reagents and to control the thermal unit 6 for heating and cooling operations as a function of the specified process parameters. In an embodiment, the automatic control system may for instance comprise a commercially available electronic PID controller and parameters of the automatic control system can be adjusted using computer software.

Referring to the figures, in particular FIG. 2, a method for in situ temperature-induced antigen retrieval of samples immobilized on a sample support, according to an embodiment of the invention, may advantageously comprise the steps of:
(i) providing a sample 1 immobilized on a sample support 12;
(ii) providing a microfluidic device 8 comprising a microfluidic chamber 40, at least one fluid inlet 32 at one end of said microfluidic chamber and at least one fluid outlet 34 at another end of said microfluidic chamber configured to conduct a fluid supplied under pressure from a fluid feeding system 10 through the microfluidic chamber 40 for transport of fluidic substances and reagents inside said microfluidic chamber in a uniform manner, wherein at least one wall of the microfluidic chamber is formed by the sample support 12 and is mounted against a seal 42 in a fluid-tight and removable manner to the other wall 33 of the microfluidic chamber 40 by a clamping mechanism 16 and wherein the volume of the microfluidic chamber is between 2.5 µL and 200 µl;

(iii) mounting said microfluidic chamber and said sample support together in a fluid-tight manner with the sample 1 facing the inside of the microfluidic chamber 40;

(iv) carrying out a temperature-controlled antigen retrieval step S1 at a pressure higher than the atmospheric pressure, wherein said step comprises:

filling the microfluidic chamber 40 with an epitope unmasking solution through the fluid inlet 32 at pressure $P_{chamber}$ in the microfluidic chamber 40 comprised between 1.5 to 5 bars;

heating the microfluidic chamber to an incubation temperature setpoint ($T_{AR}$) and maintaining the temperature of the microfluidic chamber to this said incubation temperature setpoint for an incubation period duration $t_i$;

cooling the microfluidic chamber to a cooling temperature below the said incubation temperature setpoint and higher or equal to room temperature for a cooling period duration $t_c$, wherein said incubation temperature setpoint $T_{AR}$ is comprised between about 60° C. to 200° C., incubation period duration $t_i$ is comprised between about 0.5 to 30 min and cooling period duration $t_c$ is comprised between about 1 to 30 min.

According to a further aspect is provided a method for in situ temperature-induced antigen retrieval of samples immobilized on a sample support according to the invention, wherein the said immobilized sample is subsequently stained, in particular immunostained and imaged on the same sample support.

According to a further aspect is provided a method for in situ temperature-induced antigen retrieval of samples immobilized on a sample support according to the invention wherein said method further comprises after the temperature-controlled antigen retrieval step S1, the steps of:

(v) injecting in sequence a plurality of reagents, including at least one imaging probe, through the fluid inlet into the microfluidic chamber, at a flow rate in a range between about 1 µl/s and about 100 µl/s;

(vi) imaging a signal emitted by components of the sample reacted with said at least one imaging probe (S4);

wherein said injecting in sequence a plurality of reagents includes:

an elution step (S2, S2') where an elution buffer is injected for removing undesirable material such as antibodies potentially remaining on the sample from the previous cycle;

a sample labelling step where an imaging probe is injected (S3 comprising S3', S3" etc.); and wherein each of these steps may be preceded by an optional washing step wherein a washing buffer is injected.

According to another further aspect, is provided a method for in situ temperature-induced antigen retrieval of samples immobilized on a sample support according to the invention wherein said method further comprises after step (vi):

(vii) an elution step (S0) where an elution buffer is injected for removing undesirable material such as labelling probes (e.g. antibodies or markers) potentially remaining on the sample;

(vi) repeating steps (iv) and (vii) with different imaging probes.

According to one aspect, the decreasing of the temperature of the microfluidic chamber to a temperature below the said incubation temperature setpoint can be achieved either by turning off the heating unit 24 (natural or passive cooling) or by forced or active cooling with the cooling unit 28, for instance by flowing cooling fluid in the channels 56 of the cooling block 54. The rate of flow of cooling fluid may be used to control the degree of cooling. The cooling unit 28 may be controlled by setting the temperature control system to reach a cooling temperature setpoint ($T_c$) during a cooling period according to a temperature decrease profile i.e. by setting cooling time, cooling step size, slopes (active cooling). The cooling period can be of a discrete nature, comprising two or more temperature increments down (to a first and subsequent cooling temperature setpoints ($T_c$)). In other embodiments, the cooling period is discretized up to a first cooling temperature setpoints ($T_c$) before continuing the cooling with natural cooling.

In an embodiment, a first cooling temperature setpoint value ($T_a$) is selected from a range between 40° C. and 200° C., wherein said cooling temperature setpoint value is lower than the incubation temperature setpoint, in particular from about 40° C. to about 60° C. For example, it can be about 50° C., 60° C., 70° C., 80° C., 90° C., 100° C., 120° C., 140° C., 160° C., 180° C. or 200° C.

In an embodiment, the inner pressure value of the microfluidic chamber is ($P_{chamber}$) is comprised between about 2 to 5 bars such as 2, 2.5, 3, 3.5, 4, 4.5 or 5 bars. In a preferred embodiment, it is between 1.5 and 3 bars, in particular between 2 to 3 bars.

In another embodiment, the incubation temperature setpoint value ($T_{AR}$) comprised between about 60° C. and about 200° C. For example, it can be about 60° C., 70° C., 80° C., 90° C., 95° C., 100° C., 110° C., 115° C., 120° C., 140° C., 160° C., 180° C. or 200° C. In a preferred embodiment, it is between 110° C. and 140° C.

In another embodiment, the duration of the incubation period ($t_i$) is typically between 2 and 20 minutes, in particular 2 to 5 or 5 to 10 min. For example, it can be about 2 minutes, 2.5 minutes, 4 minutes, 5 minutes, 10 minutes or 20 minutes. It is advantageous to keep $t_i$ as short as possible if the same desired effect can be achieved so that the overall sample processing time is kept low.

In another embodiment, the pH value of the epitope unmasking solution is higher than 5.5. For example, the epitope unmasking solution can have a pH of 6 or a pH of 9. Optimal AR conditions can be obtained with different buffer compositions. For example, a sodium citrate buffer with a pH of 6 containing Tween 20 (as used herein, Tween 20 is a brand name of the substance polysorbate 20) or a Tris-EDTA buffer with a pH of 9. In other embodiments, more acidic solutions (e.g. with a pH smaller than 5) can also be used as the epitope unmasking solution.

In one embodiment, the imaging probe is a labelled probe suitable for interacting with specific molecular entities on the sample. For example, an imaging probe can be a labeled RNA or DNA sequence useful for hybridizing in-situ with RNA or DNA sequences from the sample (complementary sequences). In another example, the imaging probe is a labeled primary antibody (e.g. fluorescent), which binds directly the target antigen.

In another embodiment, the imaging probe results from the injection of a sequence of labelling probes such as specific antibodies and chromogen or fluorescent detection molecules, targeting the molecular entities to be analyzed within the sample. In one embodiment, the imaging probe results from a labeled secondary (e.g. fluorescent) antibody that is injected after a primary antibody.

According to a particular embodiment, the flow rate of the injected plurality of reagents is a range from about 1 µl/s to about 30 µl/s, such as from about 5 µl/s to about 30 µl/s (e.g. about 25 µl/s).

According to another particular embodiment, the height of the microfluidic chamber as defined by the distance from the sample support 12 wall to opposite wall 33 of the microfluidic chamber ranges from about 10 µm and about 300 µm, and the diagonal or the diameter of the microfluidic chamber ranges from about 100 µm and about 56 mm, forming a shallow and wide geometry.

In another embodiment, each step in the sequence of injected plurality of reagents is applied for a period of time necessary to flush out the previous solution in the solution flow step sequence from the microfluidic chamber, wherein the flush out corresponds to a concentration decrease of the previous solution down to 1% of the previously injected concentration.

In another embodiment, each step in the sequence of injected plurality of reagents is applied for a period of time necessary to increase the concentration of the injected solution up to 99% of the intended protocol concentration within the microfluidic chamber.

In an embodiment, each step in the sequence of injected plurality of reagents lasts from about 1 s to about 120 s, such as from about 5 s to about 20 s (e.g. about 10 s).

In another particular embodiment, the step of injecting in sequence a plurality of reagents includes:
  an optional blocking step (S2') wherein a blocking buffer is injected;
  an optional incubation step, where the previously injected blocking buffer is incubated with or without any flow condition;
  an optional washing step, where a washing buffer is injected;
  a sample labeling step where an imaging probe is injected (S3);
  an optional incubation step, where the previously injected imaging probe is incubated with or without any flow condition;
  a washing step wherein a washing buffer is injected (S3a);
  an optional pre-imaging step (S4') where an imaging buffer is injected;
  wherein the sample labeling step comprises injecting either directly a labeled probe or a sequence of labelling probes leading to an imaging probe.

According to a particular embodiment, the sample labeling step S3 comprises injecting a sequence of labelling probes leading to an imaging probe which comprises a first step wherein a primary antibody is injected (S3'), a washing step wherein a washing buffer is injected (S3''') and a further step wherein a labeled secondary antibody is injected (S3'').

In a particular embodiment, the sample labeling step S3 comprises a first step wherein a primary antibody is injected (SB3'), a washing step wherein a washing buffer is injected (SB3'''), a second step wherein an enzyme-linked secondary antibody is injected (SB3''), a washing step wherein a washing buffer is injected (SB3''''), and a further step where a chromogen or a fluorescent detection molecule reacting with the enzyme that is linked to the secondary antibody is injected SB3*.

In another particular embodiment, the sample labeling step comprises a first step wherein a primary antibody is injected (SB3'), a washing step wherein a washing buffer is injected (SC3'''), a second step where a post-primary antibody is injected, a washing step wherein a washing buffer is injected (SC3''), a third step wherein an enzyme linked secondary antibody is injected (SC3''''), a washing step wherein a washing buffer is injected (SC3*), and a further step where a chromogen or a fluorescent detection molecule reacting with the enzyme that is linked to secondary antibody is injected SC3**.

In another particular embodiment, the sample labeling step comprises injecting at least one labeled probe such for in-situ hybridization with some DNA/RNA material within the sample, such as a labeled RNA or DNA probe.

In a further particular embodiment, when the sample labeling step comprises injecting at least one labeled probe such for in-situ hybridization with some DNA/RNA material within the sample, the method of the invention further comprises applying temperature cycles within the microfluidic chamber required for hybridization and de-hybridization step of some DNA/RNA material within the sample with the RNA or DNA probes (complementary sequences). For example, heaters external to the microfluidic chamber or sample support can apply such temperature cycles. In-situ hybridization can be achieved for example as defined in *Modern Pathology*, 2011, 24, 613-623; doi:10.1038/modpathol.2010.228). Imaging is then achieved on the immobilized hybridization probes for RNA and DNA sequence detection (labelled complementary sequence probes).

In a particular embodiment, each step in the sequence of injected plurality of reagents comprises for each reagent two flow rate steps:
  a first flow rate step where the reagent is injected at an initial flow rate in a range between about 1 µl/s and about 100 µl/s;
  a second flow rate step where the same reagent is injected at a lower flow (typically from about 0.001 to about 1.0 µl/s) to ensure sufficient flux of the said reagent with the sample, before injecting the next reagent in the sequence.

In a further particular embodiment, the second flow rate step of a reagent lasts from about 1 min to about 30 min (e.g. from about 2 to about 15 min).

According to a particular embodiment, the duration of the second flow rate step depends on the volume the of micro fluidic chamber 40 used and the time necessary to the incubation of the reagent with the sample. For typical primary antibody molecules, a calculated incubation time of around 1 minute is required for a chamber height less than 100 µm.

In an embodiment, the imaging step (vi) is conducted by confocal fluorescence microscopy.

In an embodiment, the imaging step (vi) is conducted by fluorescence microscopy.

In an embodiment, the imaging step (vi) is conducted by bright-field microscopy.

According to a particular embodiment, a washing buffer is selected from a Phosphate Buffered Saline (PBS) and Tris-buffered Saline (TBS).

According to a particular embodiment, an elution buffer is selected from a solution with a low pH (e.g. pH 2) supplemented with a detergent (TritonX, as used herein is a brand name for octoxynol-9). The elution buffer solution may further contain high ionic salt concentrations (for example from about 0.001 M NaCl up to about 1 M NaCl) or chaotropic agents.

According to a particular embodiment, a blocking buffer is selected from sodium citrate buffer and PBS supplemented with protein (e.g. Bovine Serum Albumin or serum) and/or detergent (e.g. Tween).

According to a particular embodiment, the non-specific binding blocking step (S2) is optional.

According to a particular embodiment, the sample labelling step comprises a first step wherein a primary antibody is injected (S3'), a washing step wherein a washing buffer is injected (S3''') and a further step wherein a secondary antibody is injected (S3'').

According to a particular embodiment, the primary antibodies of the invention may be any suitable antibodies for any immunohistochemistry and immunofluorescent assays such as described in *Dabbs, Diagnostic Immunohistochemistry: theranostic and diagnostic applications*, 4$^{th}$ edition, 2014, ISBN 978-1-4557-4461-9. For example, suitable antibodies are mouse or rabbit anti-human Immunoglobulin G or Y antibodies directed against clinically relevant epitopes.

In another embodiment, the flow is applied in a continuous manner.

According to a particular embodiment, a method according to the invention comprises at least about 2 to 80 cycles of steps (iv) to (vii), in particular at least about 20 to 80 cycles of steps (iv) to (vii).

According to a particular embodiment, a method according to the invention comprises from 2 to up to about 200 cycles of steps (iv) to (vii), in particular from 2 to up to about 20 cycles or from 2 up to about 100 cycles.

According to one aspect, the method of the invention allows in-situ imaging of samples by cycle multiplexing of molecular profiling on various samples, in particular biological samples, including tissue sections, cells cultures, protein or nucleic acid preparations.

According to another aspect, the samples that are provided for analysis by a method of the invention as immobilized by different types of techniques and include formalin-fixed paraffin-embedded (FFPE) tissue samples, cryogenically fixed tissue samples, cell smears, biopsy samples and fixed cell preparations. In particular, the methods described in the present invention can be applied to samples that are fixed by cross-linking agents, such as whole tissue samples, surgical or needle biopsies of tissue types including but not limited to breast, lung, tonsil, lymph node, prostate, gut, liver or kidney. The methods can also be applied to immobilized tumor samples, including biopsies from cancers, for example breast cancer, lung cancer, prostate cancer, ovarian cancer, colorectal cancer and melanoma. The methods can also be applied to immobilized samples of fluidic nature, such as bodily fluids, for example immobilized blood samples or cell smears. The methods can also be applied to samples of microbial nature such as bacteria. Different types of sample preparation steps can be realized depending on the sample type and desired application. For example, the methods described in the present invention can also be applied to samples that are fixed by cross-linking agents which are cut into thin sections and subsequently applied to a support, such as a microscope slide. Microscope slides suitable for use with the disclosed methods include coated or charged slides, such as poly-lysine coated slides or gel coated slides. The disclosed methods may also be carried out with free-floating samples in suspension, for example by providing a closed-chamber variant of the microfluidic device with at least one surface with biological target immobilization and capture capability (such as a surface coated with recognizing molecules) and injecting the free-floating samples into the chamber.

In this alternative, the sample immobilized on a sample support used in a method of the invention is preliminary obtained by fixing a free-floating sample on a surface of a sample support which has a specific affinity for the sample.

According to another aspect, the labelling probes comprise chemical dyes, antibodies and antibody fragments, or oligonucleotides leading to an imaging probe such as in situ hybridization or amplification probes.

The above-mentioned features may be combined in any appropriate manner.

A noticeable advantage for a method of the invention is to remove the need to repeatedly mount and demount sample coverslips for conducting the antigen unmasking and for imaging, in particular through each imaging cycle, which may affect sample integrity and result in the degradation of reproducibility and prevent the full automation of such a process, which is also essential for a reproducible labelling.

A further noticeable advantage for a method of the invention is to reduce the pre-processing time and used reagent volumes for steps such as antigen retrieval, which results in a higher throughput obtained with lower reagent consumption.

Apart from sample analysis, a method according to the invention can be useful for multiplexing genetic sequence detection such as by in-situ hybridization.

Other features and advantages of the invention will be apparent from the claims, detailed description, and figures. The invention having been described, the following examples are presented by way of illustration, and not limitation.

EXAMPLES

Example 1: In Situ Antigen Retrieval and Immunofluorescent Immunostaining with Possible Multiplexing Protocol to Carry Out Successive Sample Labelling Cycles A method of the invention for in situ high-pressure temperature-controlled antigen retrieval and immunofluorescent immunostaining of samples is implemented in a device as illustrated on FIG. 1 on a formalin-fixed paraffin-embedded (FFPE) tissue sample and follows a protocol as illustrated on FIG. 2 with an optional cycle multiplexing for conducting successive sample labelling cycles.

a) Example of Sample Preparation

Different types of sample preparation steps can be realized depending on the sample type and desired application. In the present example, the sample preparation steps for FFPE tissue samples which were carried out before is described here as a typical example.

The tissue slides of biological samples are first deparaffinized manually in Histoclear™ solution and gradually rehydrated in EtOH series according to standard procedure. This procedure is performed outside a microfluidic chamber of a device of the invention ("off chip"). The sample is then ready for conducting a method of the invention as illustrated in the exemplary device discussed above in relation to the embodiments illustrated in FIGS. 1*a*-1*g* and 6*a*-6*b*. The exemplary biological sample processing device 2 is used for implementing a method of in situ antigen retrieval and immunofluorescent immunostaining according to the invention ("on-chip") where a sample 1, for example as prepared under a), is immobilized on a sample support 12 wherein said sample support is maintained against the microfluidic device 8 to form a pressure resistant fluid-tight seal around a microfluidic chamber 40 during the process as previously described.

b) Example of Preparing a Device for Implementing the Method of the Invention

First, the microfluidic chamber 40 is filled with a solution having suitable properties as a medium for antigen retrieval (antigen retrieval solution) (Step S1' on FIG. 2a) through a reagent delivery system of the device which can be actuated through a fluid delivery control system which can be automated. The pressure inside the microfluidic chamber 40 is generated at a pressure value ($P_{chamber}$) higher than atmospheric pressure (typically about 1.5-5 bars, for instance around 2-3 bars) by the fluid feeding system 10 controlled by a control system of the biological sample processing device comprising a pressure sensor (e.g. manometer).

Example 2: In Situ High-Pressure Temperature-Induced Antigen Retrieval and Immunofluorescent Immunostaining Sequence The initial in situ high-pressure temperature-controlled antigen retrieval step of a method of the invention can be started after tissue and reagent preparation.

A temperature-controlled AR treatment step (Step S1" on FIG. 2a) is conducted under high pressure (about 2 to 3 bars) through the temperature controlled system of the biological sample processing device 2 wherein the temperature in the microfluidic chamber 40 is controlled through a temperature control protocol comprising:

(i) a controlled heating period where the temperature of the microfluidic chamber is heated under control from room temperature to an incubation temperature setpoint ($T_{AR}$);

(ii) an incubation period wherein the temperature of the microfluidic chamber ($T_i$) is maintained at the incubation temperature setpoint ($T_{AR}$);

(iii) a cooling period wherein the temperature of the microfluidic chamber is cooled from the incubation temperature setpoint to a cooling temperature setpoint, wherein the cooling of the microfluidic chamber can be either natural cooling or active cooling, i.e. under control.

The incubation temperature setpoint, the cooling temperature setpoints, heating and cooling times, temperature step size, slopes will depend on the type of epitope to unmask.

A temperature control protocol is schematically represented on FIG. 2b.

Typically, the controlled heating period ($t_1$ to $t_2$) lasts from about 1 min to about 3 min, the incubation temperature setpoint is from about 80 to about 130° C., the incubation period ($t_2$ to $t_3$) lasts from about 2 min to about 20 min, the cooling period ($t_3$ to $t_4$) lasts from about 1 min to about 20 min and the cooling temperature setpoint can be either room temperature in case of natural cooling or a temperature which is about 20 to about 90% less than the incubation temperature setpoint. Exemplary temperature control protocols are provided under Examples 2 and 3.

An initial immunostaining/imaging sequence can be started during or preferably right after the cooling period. An imaging reagent sequence (comprising washing/elution solutions, blocking solutions, labelling probe solutions, etc.) used in a method according to the invention utilized to carry out successive sample labelling and imaging cycles is outlined in FIG. 2a. Such an imaging reagent sequence is successively introduced in the microfluidic chamber 40 through the fluid inlet 32 by the fluid feeding system. When the method is used in a multiplexing mode, after the first imaging step, all the steps from the antigen retrieval step to the imaging step of another target marker can be repeated as detailed below.

Figure 2A:
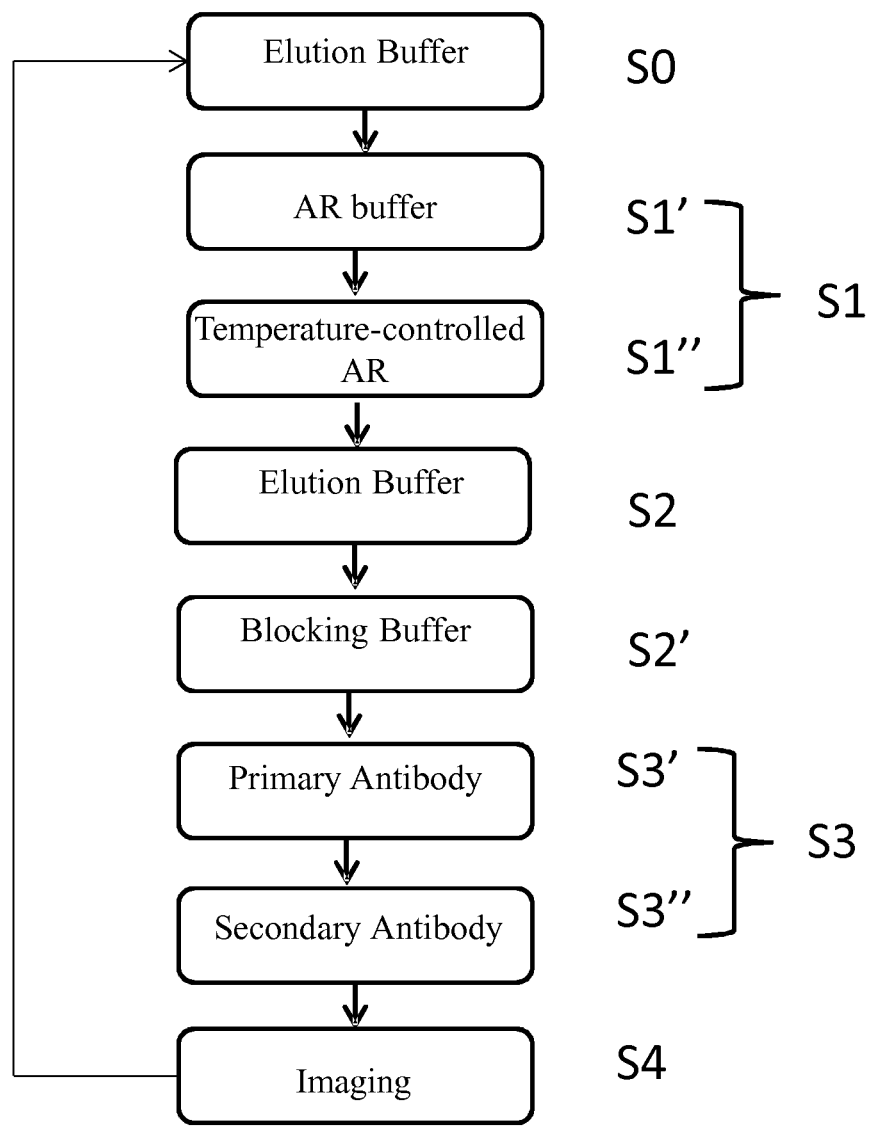
FIG. 2 illustrates a process sequence used in the in situ antigen retrieval, staining and imaging steps cycle of the method of the invention (2a), while omitting the optional washing buffer steps between each major flow steps (S1 to S4) and a temperature control protocol used under step S1 for AR (2b).

Elution Step (Step SO or S2, FIG. 2a)

Each cycle of immunostaining/imaging sequence (except the first cycle starting at S2) starts with first eluting the tissue sample by flowing an elution buffer, the composition of which and pH conditions can vary depending on the analyzed sample for removing undesirable material (e.g. labelling probes such as antibodies) potentially remaining on the sample. For example, a 0.1 M glycine buffer at pH 2 supplemented with 0.05% TritonX detergent can be used as elution buffer.

Optional Non-Specific Binding Blocking Step (Step S2', FIG. 2a)

A blocking buffer (e.g. Sodium citrate buffer or PBS-Tween with Bovine Serum Albumin) is then optionally flown in the sequence of the imaging reagent sequence through the microfluidic chamber to lower non-specific binding of proteins in the subsequent steps.

Sample Labelling Step(s) (Step S3 (S3'-S3") FIG. 2a)

The imaging probe(s) or the labelling probe(s) leading to the imaging probe are then introduced in the sequence of the imaging reagents flown in the microfluidic channel. For example, a sequence of labelling probes leading to a labelled probe includes a sequence where a primary and then a secondary antibody (labelling probes) are flown through and incubated, while washing the sample with a washing buffer between each step. The dilution ratios of labelling probes are determined depending on optimized protocol or vendor instructions.

Alternatively, another example of sample labelling step includes injecting a RNA or DNA labelled probe for in-situ hybridization. In this case, the method further includes applying a suitable temperature cycle for ensuring the hybridization of the RNA or DNA material within the sample with the complementary sequences of the RNA or DNA labelled probes.

Imaging Step (Step S4, FIG. 2a)

Imaging is performed after the end of this cycle.

The entire cyclic process (steps S0 to S4) can be repeated for up to about 50 times with different imaging probes.

Figure 3:
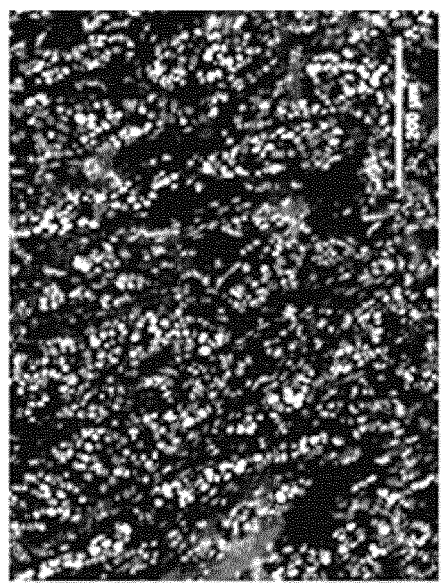
FIG. 3 shows fluorescent images of DAPI (A) and PR (B) channels and combined (C) obtained with immunostaining performed after in situ antigen retrieval as described in Example 2.
Figure 3:
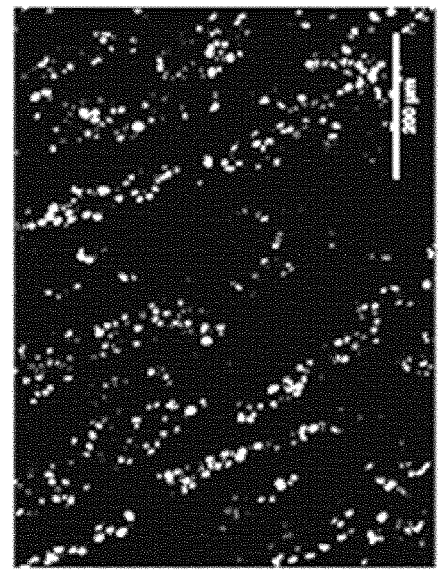
Figure 3:
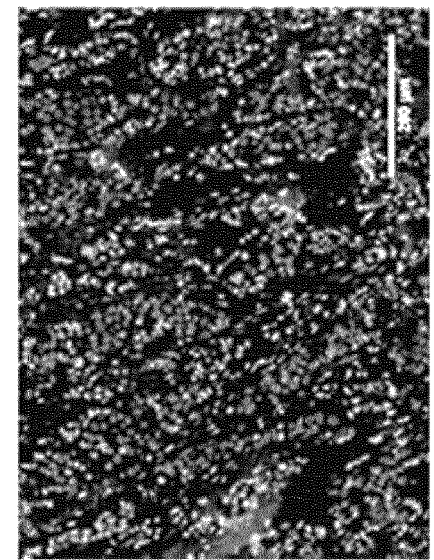

Examples of use of a method of the invention are provided herein for:

Epitope Activation for Progesterone Receptor (PR) Staining of FFPE Breast Tumor Sections Table 1 below shows an example of preparation (1,2) of the sample and its subjecting to one cycle of steps S1 to S4 (3-8) of a method of the invention to lead to staining images as shown in FIG. 3.

TABLE 1

| | Step | Reagent | Parameters | |
|---|---|---|---|---|
| Sample preparation | 1 Dewaxing | Dewaxing solution | Off-chip | 10 min |
| | 2 Rehydration | Ethanol from 100% to 0% | Off-chip | 2 min |
| AR Steps S1 | 3 AR buffer and temperature protocol under high pressure | pH 9 @115° C. at $P_{chamber}$ = 2.5 bars | On-chip | 5 min |

TABLE 1-continued

| | | Step | Reagent | Parameters | |
|---|---|---|---|---|---|
| | 4 | Cooling to room temperature | pH 9 | On-chip | 5 min |
| Sample labelling steps S2-S3 | 5 | Post-Cooling | pH 9 + Phosphate buffer sulfate | On-chip | 2 min |
| | 6 | Primary Ab | Mouse anti-PR | On-chip | 4 min |
| | 7 | Secondary Ab | Fluorescent labelled goat anti-mouse IgG | On-chip | 4 min |
| | 8 | Counterstaining | DAPI (4',6-diamidino-2-phénylindole) | Off-chip | Immediate |

The sample is prepared as described in Table 1 and the glass slide is washed again with PBS and then submerged in PBS supplemented with 0.25% Triton-X detergent for 15 min. Afterwards, the slide is inserted into a device as described herein for implementing a method of the invention.

In the present example, the duration of the overall process of the temperature-controlled AR treatment step S1 is conducted under high pressure (about 2 to 3 bars) is kept under 10 minutes as follows:
  (i) Controlled heating the micro fluidic chamber 40 from room temperature to the incubation temperature setpoint in about 2.5 minutes;
  (ii) An incubation period for incubating the sample with the AR solution at the incubation temperature setpoint for 2 to 5 minutes, and
  (iii) An active cooling of the micro fluidic chamber 40 from the incubation temperature setpoint back to room temperature within about 2.5 min to 7 min.

After the cooling period following the high-pressure temperature-controlled AR treatment step, the immunostaining/imaging of the sample is started by successively introducing in the microfluidic chamber 40 through the fluid inlet by the fluid feeding system the sequence of the imaging reagents wherein the imaging probe results from the injection of a sequence of antibodies (primary and secondary) as labelling probes as described in Table 1.

Primary antibody binding: is applied at a flow rate of 15 μl/s for 10 s and then incubated for 4 min. (S3')

Washing: PBS is applied at a flow rate of 25 μl/s for 10 s. (S3''')

Secondary antibody binding: is applied at a flow rate of 15 μl/s for 10 s and then incubated for 4 min. (S3'')

Washing: PBS is applied at a flow rate of 25 μl/s for 10 s. (S3''')

Imaging: After the immunofluorescent staining, the slides were counterstained and mounted with a coverslip to be imaged under the microscope (S4). Then, the images were visualized on Zeiss Axiovision® software and analyzed with ImageJ®. FIG. 3 shows images obtained using the described sample processing and fluorescent immunostaining methods. The DAPI channel is shown to aid in the localization of nuclei on the sample. Then, the PR channel and the combination of the two channels are separately shown. Using the temperature control-assisted methods of the invention, the sample processing times have been drastically reduced as seen in this example.

Successive Epitope Retrieval and Fluorescent Immunostaining of Multiple Markers on the Same Sample The method of the invention was used to conduct in-situ high pressure temperature-controlled AR treatment step on a sample (FFPE breast section) which has regions that co-express 4 different markers HER2 (human epidermal growth factor receptor 2), ER (estrogen receptor), PR (progesterone receptor) and CK (cytokeratin), wherein target epitopes were reactivated between each step under a pressure of about 2 to 3 bars according to a method of the invention as follows:

The pre-processing of the sample was performed outside the microfluidic device wherein deparaffinization of the sample was performed as described above for the breast tumor sections. Table 2 summarizes the specific protocol of the method which was used.

However, in this example, the first temperature-controlled AR treatment step was conducted ("off-chip") before staining outside of the microfluidic device according to a standard procedure in a hot bath of 95° C. with an incubation of 40 minutes to investigate the sole effect of the temperature-controlled AR treatment step between the staining cycles to reactivate the epitopes.

Iterative immunostaining of the sample was then carried out on the sample after the temperature-controlled AR treatment by 4 cycles of Tyramide Signal Amplification (TSA)-based fluorescent immunostaining and the immunostaining was carried out in situ within microfluidic device for the sample on which is applied the method of the invention under the conditions listed in Table 2 below. After the fourth biomarker was stained, the sample was counterstained using SlowFade Gold™ for the visualization of cell nuclei.

TABLE 2

| | Step | Reagent | Parameters | |
|---|---|---|---|---|
| Sample preparation | 1 | Dewaxing | Histoclear ™ | 10 min |
| | 2 | Rehydration | Ethanol from 100% to 0% | 2 min |
| | 3 | Antigen retrieval | pH 9 @ 95° C. | 40 min |
| | | | Cycle 1 | |
| Sample labelling steps S3 Imaging Step S4 | 4 | Primary Ab | Mouse anti-CK | 2 min |
| | 5 | Secondary Ab | ImmPress A-mouse-HRP RTU | 2 min |
| | 6 | Imaging probe | TSA AF 594 | 2 min |
| | | | Cycle 2 | |
| Elution Step S0 AR Steps S1 | 7 | Elution | EB + SDS 0.5% | 2 min |
| | 8 | Antigen retrieval | pH 9 Tris/EDTA at 60° C. at $P_{chamber}$ = 2.5 bars | 2 min |

TABLE 2-continued

|  | Step | Reagent | Parameters |  |
|---|---|---|---|---|
| Sample labelling steps S3 | 9 | Primary Ab | Mouse anti-PR | 2 min |
|  | 10 | Secondary Ab | ImmPress A-mouse-HRP RTU | 2 min |
| Imaging Step S4 | 11 | Imaging probe | TSA AF 647 | 2 min |
| Cycle 3 | | | | |
| Elution Step S0 | 12 | Elution | EB + SDS 0.5% | 2 min |
| AR Steps S1 | 13 | Antigen retrieval | pH 9 Tris/EDTA at 60° C. at $P_{chamber}$ = 2.5 bars | 2 min |
| Sample labelling steps S3 | 14 | Primary Ab | Rabbit anti-HER2 | 2 min |
|  | 15 | Secondary Ab | ImmPress A-rabbit-HRP RTU | 2 min |
| Imaging Step S4 | 16 | Imaging probe | TSA AF 488 | 2 min |
| Cycle 4 | | | | |
| Elution Step S0 | 17 | Elution | EB + SDS 0.5% | 2 min |
| AR Steps S1 | 18 | Antigen retrieval | pH 9 Tris/EDTA at 60° C. at $P_{chamber}$ = 2.5 bars | 2 min |
| Sample labelling steps S3 | 19 | Primary Ab | Mouse anti-ER | 2 min |
|  | 20 | Secondary Ab | ImmPress A-mouse-HRP RTU | 2 min |
| Imaging Step S4 | 21 | Imaging probe | TSA AF 350 | 2 min |
|  | 22 | Counterstaining | SlowFade Gold | Immediate |

Images were then acquired on a confocal microscope in four separate channels corresponding to the wavelengths of the imaging probes: 350, 488, 594 and 647 nm.

It was seen that the intermediate antigen retrieval treatment method of the invention allowed to proceed to the next staining cycle within a short time, which in turn resulted in each cycle to be reduced to about less than 10 minutes, while achieving a performant multiplexed labelling of the sample.

Example 3: In Situ Antigen Retrieval and Fluorescent Immunostaining of a FFPE Breast Tumor Section for HER2

Figure 4A:
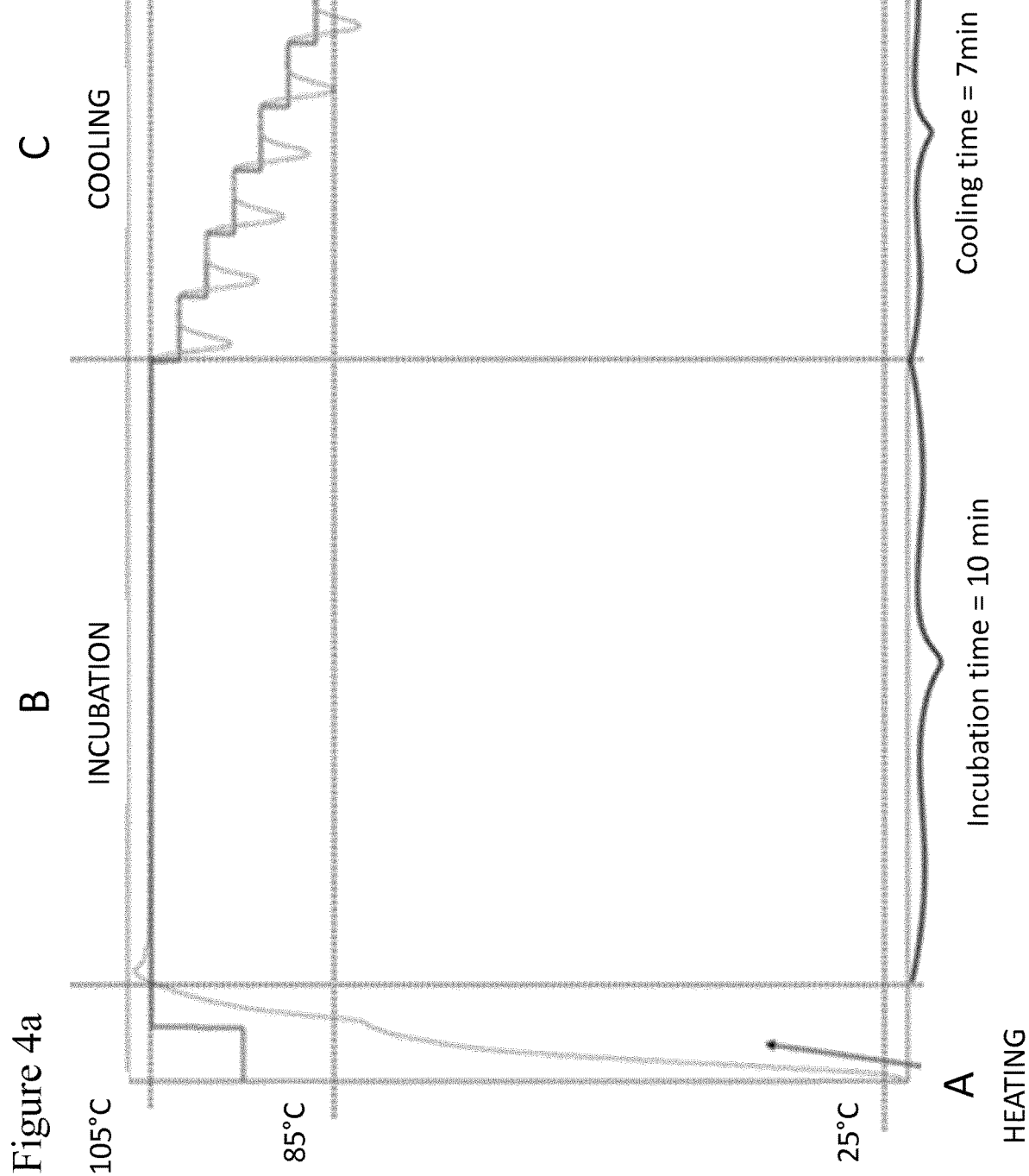
FIG. 4 shows various temperature control protocols used in the temperature-controlled AR treatment step of a method of the invention as described in Example 3; a: heating from room temperature to 105° C. in about 1 minute, incubation for about 10 min at this temperature and cooling by 3° C. to 85° C. over about 7 minutes and cooling to room temperature; b: heating from room temperature to 98° C. in about 1 minute, incubation for about 10 min at this temperature and cooling by 3° C. to 85° C. over about 4 minutes and cooling to room temperature.

The antigen retrieval method of the invention was used for HER2 epitope activation from an FFPE breast section immobilized on a standard slide according to two different protocols as follows:

The sample has been pre-processed as in Example 2 (deparaffinization and gradual rehydration in EtOH). Then, an AR solution with a pH of 6 (ThermoScientific L pH6) was filled in the microfluidic chamber and two different temperature control protocols have been applied to the temperature control elements as can be seen in FIGS. 4a and 4b. In the first protocol, the AR solution was incubated over the sample for 5 to 10 minutes at 105° C. Then, the chamber was gradually cooled using the temperature control system with 1-minute steps of 3° C. until 85° C., followed by a fast, active cooling step until room temperature is reached (FIG. 4a). The second protocol shows another variant where the sample was incubated with the AR solution at 98° C. for 10 minutes, followed by a controlled 4-steps cooling and a fast cooling step (FIG. 4b).

Example 4: Comparison of the In-Situ Antigen Retrieval Method of the Invention with Standard Antigen Retrieval on FFPE Breast Tumor Sections The in-situ high pressure temperature-controlled AR treatment method of the invention was compared with a standard AR procedure in a hot bath using FFPE breast section samples. Each sample was stained for one of the 4 different markers after the AR treatment step: (HER2 (human epidermal growth factor receptor 2), ER (estrogen receptor), PR (progesterone receptor) and CK (cytokeratin) and then the image quality and contrast were analyzed and compared.

The AR treatment for the control samples was performed in a hot bath of 95° C. with in an incubation time of 30 mins. The samples treated with an AR method of the invention were subjected to the AR protocol described in Example 1.

The staining protocols were kept identical for the samples treated with the two different AR protocols. The protocol defined in Example 1 was used with the sole difference being the use of an HRP-based chromogenic detection element instead of fluorescent secondary antibodies.

Figure 5:
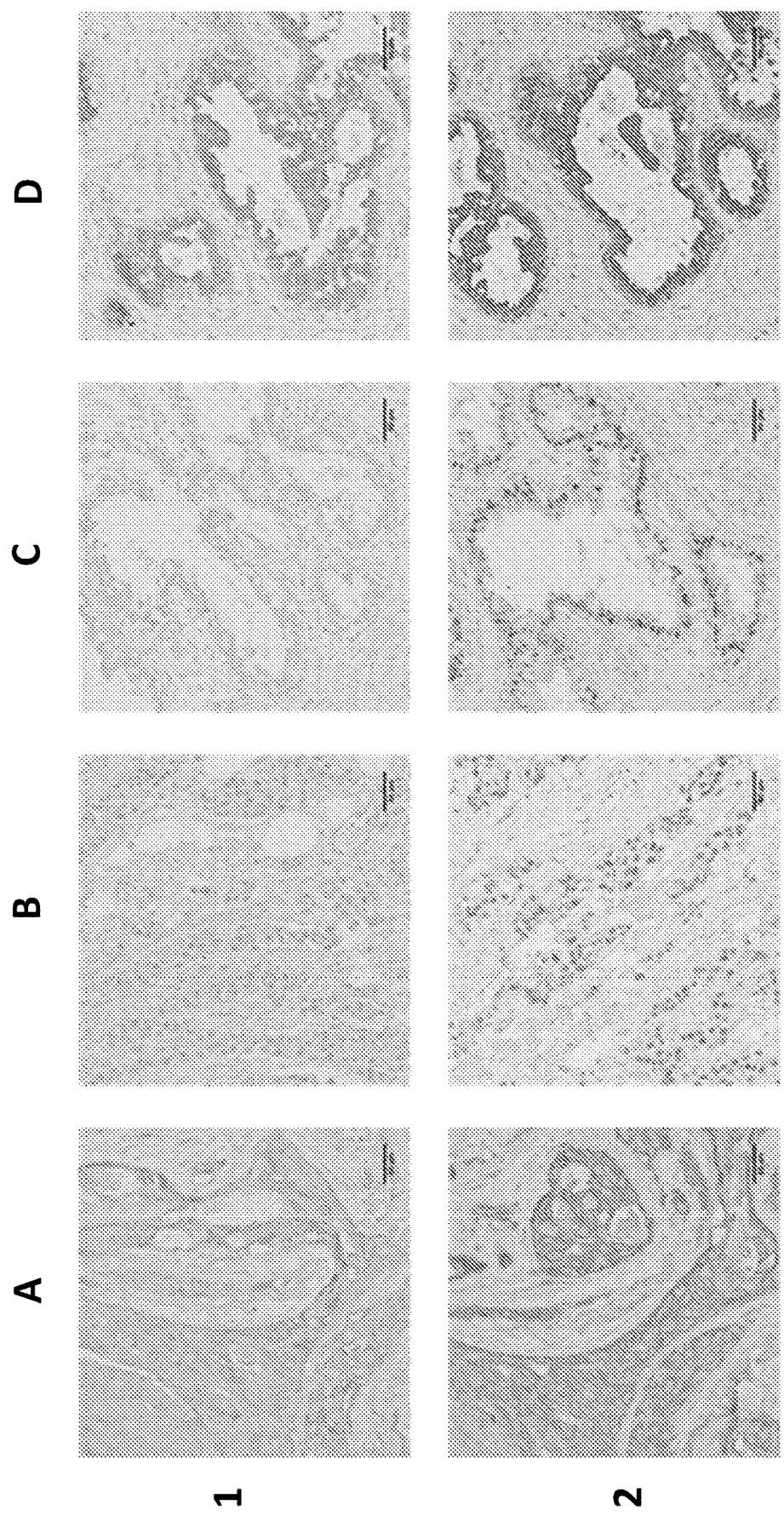
FIG. 5 shows the consecutive images obtained during colocalized staining of Example 4 of the various biomarkers on a breast cancer tissue section subjected before immunostaining to (1) a standard temperature-induced antigen retrieval procedure or to (2) in situ antigen retrieval and elution steps according to a method of the invention. The image order A to D corresponds to the acquisition order indicated in the protocol.
Figure 6B:
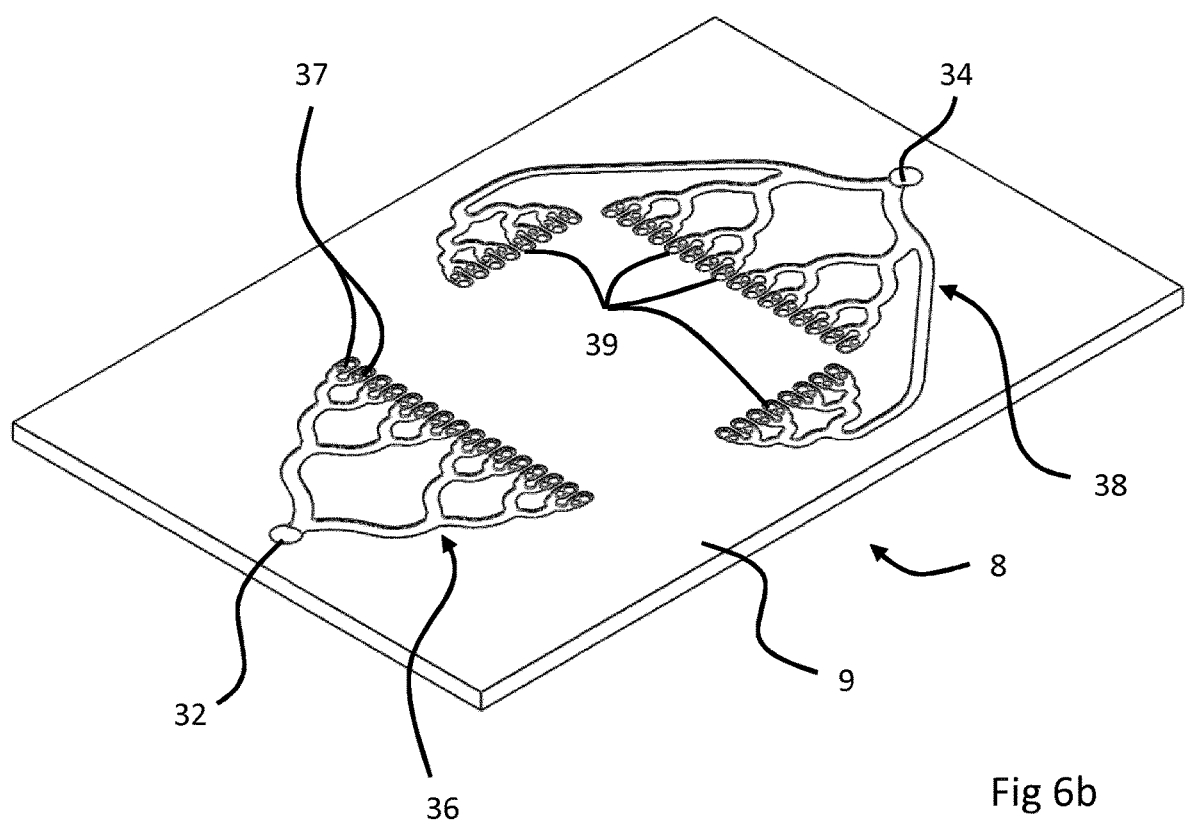
FIG. 6b is a view in perspective of a section of the microfluidic device through line VIb-VIb of FIG. 6a, showing a microfluidic channel network for the inlet and outlet of fluids into a microfluidic chamber.

FIG. 5 shows that there is at least a one-fold increase in the contrast for each of the stainings for the different biomarkers and thus that the image quality is much higher than the staining performed in a standard manner after off-chip AR, while the process duration of the invention was substantially shortened (about 5 minutes of high-temperature incubation as opposed to 30 minutes).

LIST OF REFERENCES USED IN THE FIGURES

Sample 1
Biological sample processing device 2
  support mechanism 4
    base structure 14
    clamping mechanism 16
      clamping plate 18
        viewing passage 20
        spacer 19
      actuation lever mechanism 22
        hinge linkage 17
    mounting device 50
      movable piston 51
      compressed air inlet 53
  thermal unit 6
    heat transfer unit 24
      passage 25
    heating unit 26
      Peltier device
    cooling unit 28
      cooling fluid inlet/outlet 30
      cooling block 54
        fluid flow channels 56 microfluidic device 8
  substrate 9
    first face 33
    second face 35
    fluid inlet orifice 32
    microfluidic inlet channel network 36
      chamber inlet orifices 37
    microfluidic chamber 40
    microfluidic outlet channel network 38
      chamber outlet orifices 39
    fluid outlet orifice 34
  seal 42
fluid feeding system 10
  pump and valve system (not shown)
  fluid supply channel 44
    seal 48
  fluid exit channel 46
    seal 48
sample support 12
control system
  temperature control system
    temperature sensor(s)
  pressure control system
    pressure sensor(s)

The invention claimed is:

1. A method for in situ temperature-induced antigen retrieval of a biological sample immobilized on a sample support, comprising the steps of:
   a) providing said biological sample immobilized on said sample support;
   b) providing a biological sample processing device comprising a support mechanism, a thermal unit, a microfluidic device, a pressurized fluid feeding system, and a control system, the microfluidic device comprising a microfluidic chamber, at least one fluid inlet at one end of said microfluidic chamber and at least one fluid outlet at another end of said microfluidic chamber configured to conduct a fluid supplied under pressure from a fluid feeding system through the microfluidic chamber, wherein at least one wall of the microfluidic chamber is formed by the sample support and is mounted against a seal in a fluid-tight and removable manner to a first wall of the microfluidic chamber by a clamping mechanism and wherein a volume of the microfluidic chamber is between 2.5 μL and 200 μL, wherein the support mechanism comprises an adjustable piston mechanism pushing the sample support from below against the microfluidic device to improve clamping and fluidic sealing with the seal compressed between the microfluidic device and the sample support;
   c) mounting said microfluidic chamber and said sample support together in a fluid-tight manner with the sample facing an inside of the microfluidic chamber;
   d) carrying out a temperature-controlled antigen retrieval step S1 at a pressure higher than the atmospheric pressure, wherein said step S1 comprises:
     filling the microfluidic chamber with an epitope unmasking solution through the fluid inlet at a pressure $P_{chamber}$ in the microfluidic chamber above atmospheric pressure
     heating the microfluidic chamber until a temperature of the microfluidic chamber reaches an incubation temperature setpoint ($T_{AR}$) and maintaining the temperature of the microfluidic chamber at said incubation temperature setpoint for an incubation period duration $t_i$ ;
     cooling the microfluidic chamber by a cooling unit to a cooling temperature below the said incubation temperature setpoint and higher or equal to room temperature for a cooling period duration $t_c$,
   wherein said incubation temperature setpoint $T_{AR}$ is comprised between about 60° C. to 200° C., pressure $P_{chamber}$ in the microfluidic chamber is greater than 1.5 bar, the incubation period duration $t_i$ is comprised between 0.5 to 30 min, and the cooling unit is a cooling block comprising a labyrinth of fluid flow channels for a cooling fluid to flow therethrough in order to provide active cooling of the sample support.

2. The method according to claim 1, wherein the cooling period duration $t_c$ is comprised between 1 to 30 min.

3. The method according to claim 1 wherein the incubation temperature setpoint $T_{AR}$ during the temperature-controlled antigen retrieval step S1 is comprised between 110° C. and 200° C.

4. The method according to claim 1 wherein the pressure $P_{chamber}$ in the microfluidic chamber during the temperature-controlled antigen retrieval step S1 is comprised between about 2.5 to 5 bars.

5. The method according to claim 1 wherein the incubation period duration $t_i$ is comprised between 2 to 20 min.

6. A method for in situ imaging of samples by cycle multiplexing comprising the steps of implementing the method of claim 1, further comprising the steps of:
   e) injecting in sequence a plurality of reagents, including at least one imaging probe, through the fluid inlet into the microfluidic chamber, at a flow rate in a range between about 1 μ/s and about 100 μ/s;
   f) imaging a signal emitted by components of the sample reacted with said at least one imaging probe;
   g) repeating steps (e) and (f) with different imaging probes.

* * * * *